United States Patent
Gebhart et al.

(10) Patent No.: US 12,060,392 B2
(45) Date of Patent: Aug. 13, 2024

(54) ENTEROCINS AND METHODS OF USING THE SAME

(71) Applicant: PYLUM BIOSCIENCES, INC., Lewes, DE (US)

(72) Inventors: Dana Gebhart, San Francisco, CA (US); Dean Scholl, Burlingame, CA (US)

(73) Assignee: PYLUM BIOSCIENCES, INC., Lewes, DE (US)

( * ) Notice: Subject to any disclaimer, the term of this patent is extended or adjusted under 35 U.S.C. 154(b) by 0 days.

(21) Appl. No.: 17/223,549

(22) Filed: Apr. 6, 2021

(65) Prior Publication Data
US 2021/0309703 A1 Oct. 7, 2021

Related U.S. Application Data

(60) Provisional application No. 63/006,376, filed on Apr. 7, 2020.

(51) Int. Cl.
*C07K 14/195* (2006.01)
*C12N 15/75* (2006.01)
*A61K 38/00* (2006.01)

(52) U.S. Cl.
CPC .......... *C07K 14/195* (2013.01); *C12N 15/75* (2013.01); *A61K 38/00* (2013.01)

(58) Field of Classification Search
None
See application file for complete search history.

(56) References Cited

PUBLICATIONS

Matos et al. Enterococcus faecalis prophage dynamics and contributions to pathogenic traits, PLoS Genet., 2013, 9(6): el003539) (Year: 2013).*

* cited by examiner

*Primary Examiner* — Xiaoyun R Xu
(74) *Attorney, Agent, or Firm* — Sughrue Mion, PLLC

(57) ABSTRACT

The present disclosure relates to the identification, cloning, and expression of a genetic locus within an *Enterococcus* genome that encodes a phage tail-like bacteriocin (PTLB), termed an enterocin. Also provided are non-natural enterocins, which have been engineered to have altered bactericidal specificity. Nucleic acid molecules encoding natural or non-natural enterocins, vector constructs containing such nucleic acids operably linked to a heterologous promoter, producer cells containing such vectors, the encoded enterocins, as well as methods of making and using such enterocins are described.

33 Claims, 6 Drawing Sheets
Specification includes a Sequence Listing.

FIG 3.

| Strain | AV-S32 | Av-ENcun41 |
|---|---|---|
| M27 faecium | ++ | - |
| M28 faecium | - | - |
| M29 faecium | - | - |
| M30 faecium | - | - |
| M31 faecium | ++ | - |
| M32 faecium | ++ | - |
| M33 faecium | + | - |
| M34 faecium | - | - |
| M35 faecium | - | - |
| S25 faecalis | - | ++ |
| S29 faecalis | - | ++ |
| S30 faecalis | - | ++ |
| S31 faecalis | - | ++ |
| S32 faecalis | + | - |
| S33 faecalis | - | ++ |
| S34 faecalis | - | - |
| S35 faecalis | - | - |
| S36 faecalis | - | - |
| 108 faecalis | + | - |
| 109 faecium | + | ++ |
| 13589 faecium | - | ++ |
| 13590 faecium | ++ | ++ |

SEQUENCE LISTING

<160> NUMBER OF SEQ ID NOS: 24

<210> SEQ ID NO 1
<211> LENGTH: 14629
<212> TYPE: DNA
<213> ORGANISM: Enterococcus faecalis

<400> SEQUENCE: 1

| | | | | | |
|---|---|---|---|---|---|
| ttaagttaac | ccagtattta | ataccatcac | agaataatcc | ctaaattcaa | aaatccgtcc | 60 |
| tttataaaga | taagtggcgc | catacttttg | tcgatagtac | gtaatcacat | ttttaatgt | 120 |
| ttcaacatcg | atttccaaaa | attcagcaca | agaataatgg | ttacttaagc | cagcttcaga | 180 |
| gcaacgaatt | aaatcgtcta | atgtaactaa | ttgctctaag | gccacattgc | gagctttcaa | 240 |
| ctcttgcttc | cgatttcctg | tacaattttg | atttaaaata | gtgccaacgg | atgtttgata | 300 |
| atgcccgtat | tcctcggcta | aaatattctt | cttttgacgg | gtactcaatg | ttttttcaat | 360 |
| ataaattttg | ccatttcgat | acaacccata | acaacctgtt | tgattgtata | aatcaatttc | 420 |
| taaaaccgtc | acatccttt | gaatggaact | gacgagtttt | tcataatcat | tcactttacc | 480 |
| attcacctgc | cattacttaa | taaaaagagt | agatgggaag | ttaatcctct | tttttgtcag | 540 |
| aagaaatcga | ttgttgatat | ttggcatcaa | tttcatccaa | gtaatcgtga | attttctcga | 600 |
| tctcttcttt | tgaaaatatc | ttttctggat | ccccagcgtg | ggcagccagt | gtcatttcgt | 660 |
| cacggcgagg | gaatgagaga | atttctgctt | gcgtttgttg | ttcgtgtaat | tgttgttcgg | 720 |
| caaattgata | aacgatggct | tgtcgttggg | gttctaattt | tttataaatg | cggtcgatag | 780 |
| ttgaggcatt | ttttccatg | ggaacttctt | gtcccatcaa | ccaggcctca | ttaatgtcta | 840 |
| atgcatctgc | aatgcgataa | actttgtctt | gttttgcttc | gtaacgacca | gctagccaat | 900 |
| cgctgatcga | agatttaccg | atgccagttt | ttttcgctaa | atcactaggt | tgatgttct | 960 |
| tggctgttaa | agcctctttt | aaacggacag | caaaaatgtt | catatttccg | aacctcctat | 1020 |
| tgcctcaaag | tatactatac | ctgtttagag | aaggcaagta | acaatcgcaa | ttaaatttag | 1080 |
| aagttcataa | aacccaactt | atgagttgac | agtgaaaata | tttgatgcta | agatagagcc | 1140 |
| attcaaatgt | tcggttaact | gaactaattt | ttttgaacac | tttgttcggg | aaaccgtatt | 1200 |
| ttggtgggaa | gggtgaagaa | atgagtcgga | attataaaaa | aacgttgtcg | gatatgttac | 1260 |
| ttttagcaat | tatttatta | ataagcagtg | tctcaataaa | aattggggcc | atcgtgattg | 1320 |
| gtatgattgg | cctcatggaa | ttactaacag | agtaacaata | atttagtcaa | aaggagagaa | 1380 |
| gcggattggc | agaacgacgc | atgtttgcaa | aaacgattat | tgatagtgat | gcgttttag | 1440 |
| atatgcccctt | atcaagtcag | gctctgtatt | ttcatttagc | gatgcgtgcc | gatgatgatg | 1500 |
| gatttatcaa | taatcccaaa | aaattgcagc | gaatggtcgg | ttgtggggaa | gacgatctaa | 1560 |
| aattgttgat | ggttaaaaaa | tttattctag | tatttgaaag | tggtgtgatc | gttatcaaac | 1620 |
| attggaaaat | tcataattat | attcgcagtg | atcgttacaa | accaaccttg | tatcaagaag | 1680 |
| agaaaaatca | gattgttgaa | aaaaatagca | aagcttatac | gtttaaagca | gaatcgtctg | 1740 |
| tcggtggtca | accagctgac | taccaacggt | taccacagga | aagcatagtc | cagtctaagt | 1800 |
| taggtcagag | tcaaggcagt | agttcagaaa | acgattgttt | aaagatgatt | tatcattttt | 1860 |
| atgaggaaaa | cggctttggt | acactggcct | caaaaacaag | ccaagatttt | aagtattggt | 1920 |
| tgcaagattt | tatacaaaaa | ggggctagcc | aagaggaagc | atgccaatta | atcttgcatg | 1980 |
| ctttaggaat | tgccgtcgat | cgaaataaac | ggaattacgg | ctatgtaaat | gctattttga | 2040 |
| aaagttggga | gcaacaaaat | tatttatccg | tacatgaagt | tctggtaaat | gataaaaaac | 2100 |

```
aagtgttgga gcatgcgccg caaatgacag aagaatatca agagttaggt ttttaaagaa    2160
aggaggaaat cagtatgcat gcgacagatc aaacttttca aatactattg agtcaattgt    2220
tagaaaaagt tgaagaccgt tgtcctgaat gtggcagtga acaatatgtt tggcaacaaa    2280
aaaataaaga tggcacagaa cgttgtgccc caacttgttg gtcgtgtggg tataaaatgc    2340
taaaaaaaca tgaacaacaa gccaatcaac aacgttctca agagagtttt atggcacgta    2400
cacaaaaatt ttttcatcaa gggtccttaa ttgctgatga tgcgctacgg caatgtcgtt    2460
taaccaatta ccaaaccact gaattagaaa caagacaagc aaaagaacgg gccttagcag    2520
cagtttcagc gattgttgaa ggaaagccaa tccacgttat tttttcaggg aaacctggtg    2580
tcggtaaaag tcatttggct atcagtattt tagttgaagt cttagaacgc tctgcatatc    2640
aaaagtattt tttatttgtc agctactctg agttattaga aaaactaaaa atgtccatga    2700
atgaatcggc caaaagccaa gcaaaggctc aagcgtatat tactagaatg aaaaaagcag    2760
acgttttggt tttagatgat ttaggtgctg aattaggaat taaaaataaa gttagtacgg    2820
attttaataa tgacatctta aaccgaattt tagaagctag acagaataaa gcaactattt    2880
ttactactaa tttttctgga aaacaactgg tggaggccta tggaacacgc attatttctc    2940
gtctaatgaa gcacgccaat ggctatgttt tccaatataa agacacaaca gacaaacgaa    3000
tgaggagtgt gaaataaata tgttaacaat tattattggg tttatctttt ggacaatgac    3060
actaatgtta ggttatctaa ttggtgaaag agaaggccgt aaacatgagt aatttaacaa    3120
aacgtaaaaa agatttattt gaaatgaaaa gcgttgtatt taaagatatt tcaaagcaac    3180
aaagcgaaaa agcacaaaaa agaaaacgac tcttacaact aatgaatcaa tatcccgatt    3240
gggcaagtca aaaaaataaa cttattatgc aggaaattca agaattagga caagcaatcg    3300
gtaattggtc gatggatcaa tcaagaccca tccaatccat caaggccgca tcgtttacaa    3360
aaagcgagta tctctatttta atttggctcg gttattcaga tgaagcgatt cgtcacggct    3420
tagacatgtc gaaagagtgt tattttattt atcgattaac acttttaaat gaataaaagt    3480
aaaggagatt aaccaatgcg tacgtcaaca tttaattata tcaaagatat tttagcagac    3540
ttttataaaa cagaagagta tatccgtcaa cgggaagaag aattacggca cccttatcaa    3600
gaagcagatt taaatgctgg tattagagga caaggacttc actctgtagt gaccgaacga    3660
atggcgatta cgatagctat ggatcgtcgt ctgtggaact tagagagaaa tcgagacatt    3720
atcaaaaatt gtttagccga agcggatgaa caaacgcgcg tgattattga agaactatat    3780
atgaaaaaac ggccctcttt aacattaatt ggacttgccc agcaattatt tattagtaaa    3840
agccaagcct ataaattaag aaatcatttc tttgaagcgg tggcggatga actagggatg    3900
taaacatgga aaaagcgtgg aatttttttca ggtgtcaaca tggtaaatta atagtgtcga    3960
aagagataga taaacgtgag gcaaccaaaa aaatgaagac acggaattct atgattttga    4020
ctgctttctt gtgtcagcta tgaaggagca gaaaatgccg gctactttca agatccttca    4080
ttttgactag aagagagcca atttgttaac caatcctgaa ttttttgaat ggaaaggtgg    4140
cgctaaaaat gaatgaagcg gaacaagagt tatatgaagc ccttgttgca atctgccaga    4200
cgtcaggatt tttgttgcta gaggaactgc cgacagattt accagatcag ccatttgttt    4260
acttaggtga tagtaaagaa ttacctaagc caactaaatc agctattttg ggagagattg    4320
aattaataat gcatgtttat ggtgcgttat ctgaacgaca caaatttcct acaattaaag    4380
gaacgatttt acggcaggca accagtaact taaaacgaac ggctcatttt aattggggta    4440
```

```
tcaaacatca agaagtcaaa gcacaaatgg taaaagatac caaacaaatg aaaaaaacaa    4500
tttggcatgc tgtactacca ttacacatgc aattttacta ggaggaatta tcaatgggag    4560
aagttatgca aggaaaagac cgtattttat tagttcgtcg cttggatgaa gcagcgacaa    4620
agaaagcaat gaaaccctta tttcaaattg aacatgaatg ggaattctca cgtgaatcga    4680
gcggtacgca acaaaagat ggcgtcgcga atgctgtttc tggtttagaa gttacgttat    4740
cgttaagcgg tttagcctct cgagatgatg aaaatttata catgaaagac gcagtcgaag    4800
atggcatctt aatggaattt tgggatgttg atttaaaagg tgaaaaaaat gcggaaggta    4860
aatatccagc aatttatgcc caaggttatg taaattcatg gagtttacca gccaatgtag    4920
aagaattagt agaaatcgaa acagaagcct ctattaatgg caagccacaa gatggctttg    4980
caacagtaga agcagatatt attgcagaag cacaatatgc gttccaagat accgttccag    5040
ataaagcacc acaacctggc gaataatcaa aaagtgttga attttaggag gataaaaaat    5100
gaatttagag attaacggaa aaacaattga agtgaaattt acgattggcg cgattcgcga    5160
attagataaa cgttaccaaa ttgaaaatgg cgctgccaaa ttcggcatgg gcatcagttc    5220
agcaatgatt tatttacgcc aatacaatcc agtaatctta gttgacatca tggaagcttt    5280
acaaagtggg caattaaaaa taggtaagtc ggaaattgaa gcatggttaa tgacccaaga    5340
tgtcaaaaaa ctttcagatg atttgcttaa agaaatggga aagcaacctc ttacaaaacc    5400
aatgatcgat cagttcagca aagaagcgaa gaaagcagaa gcgcaagcga ccaactaatt    5460
aaaacgagcg atgacgtgta tcacgacatc gctctttctg cttttcgcta cttaggctgt    5520
cgttcatttg aagaagtgga tcagatgacc atgtctgaat tgaattacg aatgattgct    5580 tttaatttag cagaagtaga tgaagagcgg aaaaggcacg agcttgccta cttaaatgtt    5640
aaagcgcaag cgacaaacaa aaaaggaaaa cccgttttg aaagctttaa aagttttat    5700 gattatgaaa aacgagttgc tgaagttctg gcagctaacc agccacaacg aacaaaatta    5760
aatgagcgga aaaaacgca acttgccact gtggcagagc gtctacgccg ctatcgagaa    5820
gggaggagag tagatggaga atgacaaaga aaaacgccg ttatcggagg caaagaaaag    5880
ccttgcaggc gtccaacaag cattaaaaag tatgagcggt gagtatgcct tattaagtgg    5940
atatttaggg aaaattagtg cgggtgtcaa tcagtcagcc acggtcatga acacatttaa    6000
aaccgtcatg caacaatctg gagaaacagt gaaaaaaaca ggagacgaaa cagcaaaggc    6060
agcagatcaa atgaacacag cgttaacaga ttctgctgaa caagccggtg aagcagctaa    6120
aaaagcgggg aaagaaacct ctgatggctt tactaatgca caaaataata tgctgagctt    6180
tgggacggcc atgactagtg ccgtttcctt acctatgctg aacgttttaa aaacagctat    6240
gggcgtcggt gctggggtca gtggcgaatt tcaaggaatg caaggactga ttatggccag    6300
tgcaggaggg atttctgatt cattgcaagg cgagttgcaa ggggcattga ctcagatgaa    6360
tcaatcattt gaagcggcgg cacaagtgat tcaaagcgtg atggctccag gaatggaaat    6420
tttggttcaa gtggttatta cagtcgtcaa aggcattaca gctttggtta atttattat    6480 caaattacca aaacccgtcc aagttttttat tgttgccatt atgggcattt tagccgccat    6540
tgggcccatg ttgattatgg taacgatggc tcagctaaaa tttcaacagt ttagtgctgg    6600
tttggctctt gtacaaggaa acattgggaa gttaggtggt ggcttatcaa aactaagtgc    6660
tagttttagt gccttaggtg gaggaccatt aatttttaatt gtagcagccg ttttagcagc    6720
ggtagcagcg tttattttatt tctataaaac caatgaaaca tttagaaata gtatcaatag    6780
cttagctagt gccattcaag gagctgtttc agcggcgttt ggcaaattgg taggattgct    6840
```

```
acaacagatc cagccggcct tcagcaagt aatggcagtt tttaaacaat tttttgcagt    6900
aggcttagag aaaatggcga ctattttttc aacaattggt cgtgtgctag caggcgtttt    6960
tgccagcggt ttgcaattag gtagtaactt attagggcaa tttggtggca cctttgacaa    7020
agctggttta gcggttggtc ttttggtaaa agttctgaca aaggttgcac tggctgcatt    7080
aggaatttct gggccgtttg gtctaattat ttccttgatt gtttcattcg tgacggcctg    7140
gatgaaaacc ggtgatttga gtgcgggtgg tattacccaa gtctttgata atttaggtaa    7200
cacgattaca tcggttacaa caatgctggc aactaatcta ccgaaagtta tacaactttt    7260
tacaacagtc ttaaccagta ttctcgggaa aataacagaa gctattccaa gcatcgtaac    7320
cgcgttatct agtttaatta cgttaattgt tggtgcgatc gttgccaatt gccagtctt     7380 aattgaagcg gcaacacaaa ttattactac gttgattcag gggattacaa cagtcttacc    7440
aatgttgata gaagttggtt tgagcttatt aatgacttta gttaatgcga ttgtcaccgc    7500
cttgccaaca attacaactg cagcgattaa tatcatcact acattagtga cagcttttgt    7560
cacagcgtta ccaatgctag ttacagcagg tgtttcaatt atcacggcct tagtcaatgc    7620
atttgttact atgttaccgt tgattttgac tgctggttta caaattttga tggcattaat    7680
cactgggatt atgacgattt tacctcagtt aattcaatca gcgctgacga ttattctagc    7740
gttagtgaca gcgttgatag gtgccttacc acagattatc agcgcaggtg tcaaattgtt    7800
aatggcgtta attcaaggaa ttatttcgat tttaccaacc ttagttgcgg cagctattac    7860
cttaattttg acattggtaa atgccttaat tggtgccttg ccacaaatca tcagcgcagg    7920
cgtcaaattg ctaatggctt tgatccaagg gattatttca attttaccgc aactggttac    7980
tgcagcaatt acgctaatta ccgctttaat gggtgcgtta atcaatgcgt tgccacagtt    8040
gttaagtgct gggattcaac tgattcaagc cttaattaat ggtgtactca gtctattggg    8100
tgccttgctg tccgcagcag gaacattaat ctcacaaatg atcacgaaga ttggttctta    8160
ttttggtcaa ctgttagctt cgggcggaca gttagttgaa aatatcaaaa atggggttac    8220
caatgcagcc aatcaggtaa aaaatgccat tggttctgta attgaaggtg cttggcaagc    8280
aatccaaggt tggttttcaa aattcaccga tgccggtgcg aatattgtcg gcatgattgc    8340
tgatggaatt acaggcgcaa ttggaaaagc caaagaagca atcgatggag ttgtcagtaa    8400
aattcgtaac ttttttaccat tttccaccagc aaaagaaggt cccttatctg atttgcataa    8460
attgaatttc ggcggcacga ttgccacggg gatttatgca ggcgaaacag ccgttagtag    8520
agcaatggct tctatttag atttaccgct gttaaatgat tttgccttgg acttagctgg    8580
tcgaggaaac ttcacggcaa cgattgacca tcgtttagaa aatgatgcat acaatcgacc    8640
attatttgtg acagtagagt caacgttaga tggaaaagtt gtcgcagcaa ctacggcgcc    8700
ttatttagca acagagttac aacgacaaca agtgaaacaa aataaccgct taggaaggag    8760 aggataaacat gtataaattt gttgataacc atcaagcaac tcattcaacg cctcttcctt    8820
cagaagcgtt gaattttaac ggccaatttt tagaaaaagt catccctggc tatcaaacat    8880
tatcagtttc aggacgagaa ttagttccaa gcgaaattga aagctatcaa ttagggattc    8940
gtgatggtaa acgtcacgtt tatgcgcgaa ttccagaacg agaattaaca gtcaaatatc    9000
gcctttcagc tgtgaataat gaagcatttc gagatgcatt taatcattta aacgttgctt    9060
tgtttacgga aaaagacgtt tctatttggt ttaacgatga accggaaatg ctgtggtttg    9120
gcagtaagtc ttcagtgagt gatgtacccg aaggtgttaa ccaagtaaca ggcaccttta    9180
```

```
ctttattgct ttctgatccg tataaataca cacggagtga tgcgactagt gtgatgtggg    9240
gttcgccaac cattacattt caagcgaatt acttaatggg gaatacaggc tcaggtgcat    9300
ttgattttcc aattttaatt gaaggcgggg cttattgggg atcaaccatg attacctttc    9360
aaaatcgggc ttacacgatg ggggatttag gcaaagaagt tcggccaatt gaaatttatc    9420
ctacggttga aggattaaaa gtcaaaccga ccattatttt aacaggaacc ggacgtggtg    9480
tttggattaa aacacggaac gatacaatta acttaggaga cttgatcgt tcggaaatta     9540
ttatcgatac tgaaaatttt tatctgacaa aaaatggtgc accgatgatt cgaccaatga    9600
acgattttta tctatatccc aatgaaccgc tgtatattca agccaaagat agcgacttcc    9660
gcttgacgat tcgctatcct aaccgatttg tgtaggaggg tgattaaatg ttaatggcgc    9720
tggatttgaa agaacatat acggcaatct tggataatgc ctatcaagtc agttatgaaa     9780
aaatagagaa caaaattggc agtttagatt ttaccatgcc actagatgat cctaaaaatg    9840
aatttattgc agaaatgcaa tgggtggaac tgaccgacaa tgagaatgaa tatattggtt    9900
tatatcgcgt gatgccaacc acaattaaga aagatgcgaa caataatcaa attcattact    9960
ctgccacaga agcattatgt accttaggtg atactgtcct ttttggttgt cacgaaatta    10020
aaaacaaaac aacgaaagag gccattcaat ttttattgaa taaacaaaaa acaaagcatt    10080
gggtcctaaa aaaatgtgat ttttcaagga aattaaccta taaatgggaa aatgaaaatg    10140
ggttagttga gcctttattt agcatcccag ccgatttcga agaggaatat ctttggcaat    10200
ggaatacaga ggtctatcct tttgaacttt cattagtcaa accgccaaca gaaccagttg    10260
cgcgaattca agaaggttac aacatgcaag gatttgaaat agaacgtaat cccaagatgc    10320
taatcaatcg gatttatcca ttaggttcag gcgaaggtgt taacaaagtc aatattcgct    10380
cggtcaatca agggggttccg tatttagaga acaaggccgc aattgaccgc tatggtttat    10440
tggagtcaat ttgggtggaa cagcgttttt ctgatcccaa ggcattaaag gaaaatgctt    10500
tgcgaatgtt agaagaatgg accaagccac aagtttcttg ggtagtgact gcagctgatt    10560
taattaaatt aacagatcaa cctttggcaa tcgatcgttt gcggttgggc acggttatca    10620
tgattaatac gaatgaattt gggagtgtca accttcgtat taaaaagaa agcaaaaaag     10680
atgtctttgg tgcccccaa gacattcagc tagagttggg aaacctgcaa gaaacaattc     10740
atagtaccat gacagctttc agtcggaaac aagagattaa cgaaacttac gcacaagggg    10800
cgacgacact tttaaatcgt tcaatacaag gagaacttag caagacacag ccagtggagc    10860
tgaatttata ctttgacgag gacattcttt atataaacac cgcagaatta acgttcaagg    10920
caactgctaa aggaccttcg cattctgtaa cgaacattga tttggtagtg gatggcaaaa    10980
aattacccca actatcattg caacaacaac ggctaaacat tttgagttat ttacgaaaaa    11040
caacagatga aaaaatcgaa cgcggcaatc acacgcttca atttttctct catcagccac    11100
tatggttgga tgcttcggtc atctgtcgtg tgtatattca atcccaattg ggtggccagt    11160
tttaataaaa taatgaaaac tagaggagtg tgacgaaatg tcagtagaac atattgaaga    11220
attagatacc ctgaatcaag gtcgccttaa aatcaatgca atcttggatc agtcgaatgc    11280
atcagctgag aaagtagatg cttaccaagt ccagttaacg aatggaattt ctgaagcgaa    11340
aaacatagca gatgaagctg gcaaagaagc cgtacaaatt gccaccgatg caggcaatca    11400
agcaaatgaa acagccaacc aagcgatgaa caatgccaaa acagcaatca tgattgcagg    11460
aaatgcagtt tcaacggcaa ataataataa acaagaattt gatactttac gaaatgattt    11520
cgatcaatta gtagcagaag cgggtgatag taatccagaa attgtccaag cacgtacaga    11580
```

```
tacacaaggc atcaaacaag ctaccttagc gaatcgtctt caaattgatt tgaatgaccg   11640
tatgacaaaa gcagacggta tttctttatt ggctaagcca actactgtca aaatgaagtt   11700
agactttaac ggtaaaacgg ccggcaatac agccaccaat gcaaacagtt attccactga   11760
ttttacggca aaaattctta agaagccaac agaagtttgg gaggaagttt cccaagcgga   11820
ctacaataaa atggccagcc gtgatgatga gggcgtgaaa acaggttcca cccaaagcgg   11880
tgtgattccg caacaattag cggccttcaa tctcgttgaa gccgctaaaa aattaattcc   11940
acaaatgttt gaaacagtca caactgacga ggcggtggca tttattcgcc agaacgttca   12000 atttttacg attaatcaac gtgtgaaagc cgctgcgccc aataatcaaa cgattaaaat   12060
cgctacgtat ttaccaacta cggataattg ggtaactcaa atccaagaat cagcaaaaga   12120
gtttggcgat ttttcaattc aaatcaatga tcagaatttt atcacagatg aaggtttcat   12180
ttatttaatg agctatacag attcatcgaa tggggtaacg ccagctagct tagaagttga   12240
ttacgtgggg cttcatattg gtctgtctgt tgatgcccaa gcggttttag cgaagagtgg   12300
ttttgttcaa gcagagcaac tcaatacccca tatggaaaat caagataacc cgcaccaagt   12360
aaccgctgaa caagtggggc taggcaatgt agaaaaattat ggcttcgcat cagacagcga   12420
agcagtcgcg ggaactttaa cgagtaaata tatgcacccg aaaaacgttg cggaagcgat   12480
taaaggtcaa gctgtgacac aaacaggtga tcaagagatt gctggggtga agaattttgt   12540
aactatgcca accgtcaatg gtgtgccttt ggaatcctct agaatggcca tttatgaagc   12600
tagtggagtt ggtgaagtcg aggcaaaata tcaggcggcc tttaataagg ataatatgaa   12660
atttgtatta attagggtag gaaatcgtgt cgatgcattt gtaagatgta atttgagtga   12720
tccaacgaaa ttgaataata atttggttaa agtgtttact gttccaacag atatacatt   12780 atcgacgaag attacaaagg gaatatggaa tttggcgtta actgctatgc aatatacatt   12840
ccctcaaccg aattgtgctg gtttatatga gatgggaaat caaggaattc ttttggtgc   12900 taaccgtgct ggaaatattt acctacaagg aagttggtac acggacgatc cgtttccaac   12960
aaaataacaa gctagtttag gagtcttttt atggaacgtt atctcaacac aataacaatg   13020
cttttaagca ttttcggtgg gattgtcgta cgtttattag gcggattaga tcaattgttg   13080
gatgtcttcc tctttttaat tattgtcgat ttcatcacag gttggattaa ggcaatcgcc   13140
acaaaagaat tgtccagtcg gattggtatg ctcggaattg cgaaaaaagt gacgatgtta   13200
tttgtggttg ccgtagcggt tcgtgttgaa aaagttgtgg ggaacaattt gccaattcgg   13260
gaaatggttc tgattttta cattgcgaac gaaggacttc ttttttttga aaacattgcg   13320
acctttattc ctatgccgaa aaagttaaaa gagttattta ttcagttaaa aaataaagat   13380
gattaagtag aagtggtcgg acaaacgta gaactttcgg ctgattgccg aagaaattac   13440
ttctgtcccg ccatttatct gcaggtttaa gccgtggaag ggaagttatt ttgactttcc   13500
tttcatggct tttttaagaa aggagcatgc tatgtttaaa aaattaatga ttcaacttgc   13560
tttagtgatt ggtttaagtt taacgattcc gatgacggct tgcgcttaca ccatcgaagc   13620
ggatccaatc aactttactt attttcccgg ctctgcaagc aatgaattaa ttgttttaca   13680
tgaatctgga aacgagcgga acctaggacc acacagttta dacaatgaag tggcctatat   13740
gaaacgaaat tggtcaaatg cttatgtctc atattttgtc ggatctggtg gacgagtgaa   13800
acaattagct cctgctggcc aaattcaata tggcgcaggt tctttagcta atcaaaaagc   13860
ctatgcgcaa atcgaattgg ctcgaacgaa taatgcggcg acatttaaaa aagattatgc   13920
```

```
tgcctatgtt aatttggccc gtgatttggc tcagaacatt ggtgctgatt tttctctgga   13980
cgatggaaca ggttatggca tagtcactca tgattggatt acaaaaaatt ggtggggaga   14040
tcatacagat ccttatggtt atttagcgcg ttgggggatt agtaaagcgc agttggcaca   14100
agatttacaa acgggcgttt ctgaaacagg tgagactgtc attattcagc caggtaaacc   14160
taatgcgcca aaatatcaag taggacaagc aattcgtttc acttcaatct atccaacacc   14220
agatgcttta atcaatgaac atctatcagc agaggcactt tggacacaag taggaacaat   14280
tacagcgaaa ttaccggacc gacaaaacct ttaccgtgtt gaaaatagcg acatttgtt   14340 aggttatgtg aacgacggcg acattgctga actttggcgc ccgcaaacga agaaatcatt   14400
tctaattggt gtggacgaag gcattgtttt aagagcagga caacctagtc tgttagcacc   14460
catttatggt atttggccta aaaatactcg cttttattac gatacgtttt atattgcaga   14520
tgggtatgtt tttattggtg aacagatac gacaggcgcg agaatttatt tgccaatcgg   14580
accaaacgat ggcaacgcac agaatacatg gggatcattt gctagctaa             14629
```

<210> SEQ ID NO 2
<211> LENGTH: 157
<212> TYPE: PRT
<213> ORGANISM: Enterococcus faecalis

<400> SEQUENCE: 2

Met Asn Asp Tyr Glu Lys Leu Val Ser Ser Ile Gln Lys Asp Val Thr
1               5                   10                  15

Val Leu Glu Ile Asp Leu Tyr Asn Gln Thr Gly Cys Tyr Gly Leu Tyr
            20                  25                  30

Arg Asn Gly Lys Ile Tyr Ile Glu Lys Thr Leu Ser Thr Arg Gln Lys
        35                  40                  45

Lys Asn Ile Leu Ala Glu Glu Tyr Gly His Tyr Gln Thr Ser Val Gly
    50                  55                  60

Thr Ile Leu Asn Gln Asn Cys Thr Glu Asn Arg Lys Gln Glu Leu Lys
65                  70                  75                  80

Ala Arg Asn Val Ala Leu Glu Gln Leu Val Thr Leu Asp Asp Leu Ile
                85                  90                  95

Arg Cys Ser Glu Ala Gly Leu Ser Asn His Tyr Ser Cys Ala Glu Phe
            100                 105                 110

Leu Glu Ile Asp Val Glu Thr Leu Lys Asn Val Ile Thr Tyr Tyr Arg
        115                 120                 125

Gln Lys Tyr Gly Ala Thr Tyr Leu Tyr Lys Gly Arg Ile Phe Glu Phe
    130                 135                 140

Arg Asp Tyr Ser Val Met Val Leu Asn Thr Gly Leu Thr
145                 150                 155

<210> SEQ ID NO 3
<211> LENGTH: 160
<212> TYPE: PRT
<213> ORGANISM: Enterococcus faecalis

<400> SEQUENCE: 3

Met Asn Ile Phe Ala Val Arg Leu Lys Glu Ala Leu Thr Ala Lys Asn
1               5                   10                  15

Ile Lys Pro Ser Asp Leu Ala Lys Lys Thr Gly Ile Gly Lys Ser Ser
            20                  25                  30

Ile Ser Asp Trp Leu Ala Gly Arg Tyr Glu Ala Lys Gln Asp Lys Val
        35                  40                  45

```
Tyr Arg Ile Ala Asp Ala Leu Asp Ile Asn Glu Ala Trp Leu Met Gly
    50                  55                  60

Gln Glu Val Pro Met Glu Lys Asn Ala Ser Thr Ile Asp Arg Ile Tyr
65                  70                  75                  80

Lys Lys Leu Glu Pro Gln Arg Gln Ala Ile Val Tyr Gln Phe Ala Glu
                85                  90                  95

Gln Gln Leu His Glu Gln Gln Thr Gln Ala Glu Ile Leu Ser Phe Pro
            100                 105                 110

Arg Arg Asp Glu Met Thr Leu Ala Ala His Ala Gly Asp Pro Glu Lys
            115                 120                 125

Ile Phe Ser Lys Glu Glu Ile Glu Lys Ile His Asp Tyr Leu Asp Glu
    130                 135                 140

Ile Asp Ala Lys Tyr Gln Gln Ser Ile Ser Ser Asp Lys Lys Glu Asp
145                 150                 155                 160

<210> SEQ ID NO 4
<211> LENGTH: 60
<212> TYPE: PRT
<213> ORGANISM: Enterococcus faecalis

<400> SEQUENCE: 4

Met Asn Thr Leu Phe Gly Lys Pro Tyr Phe Gly Gly Lys Gly Glu Glu
1               5                   10                  15

Met Ser Arg Asn Tyr Lys Lys Thr Leu Ser Asp Met Leu Leu Leu Ala
            20                  25                  30

Ile Ile Leu Leu Ile Ser Ser Val Ser Ile Lys Ile Gly Ala Ile Val
        35                  40                  45

Ile Gly Met Ile Gly Leu Met Glu Leu Leu Thr Glu
    50                  55                  60

<210> SEQ ID NO 5
<211> LENGTH: 256
<212> TYPE: PRT
<213> ORGANISM: Enterococcus faecalis

<400> SEQUENCE: 5

Met Ala Glu Arg Arg Met Phe Ala Lys Thr Ile Ile Asp Ser Asp Ala
1               5                   10                  15

Phe Leu Asp Met Pro Leu Ser Ser Gln Ala Leu Tyr Phe His Leu Ala
            20                  25                  30

Met Arg Ala Asp Asp Gly Phe Ile Asn Asn Pro Lys Lys Leu Gln
        35                  40                  45

Arg Met Val Gly Cys Gly Glu Asp Leu Lys Leu Leu Met Val Lys
50                  55                  60

Lys Phe Ile Leu Val Phe Glu Ser Gly Val Ile Val Ile Lys His Trp
65                  70                  75                  80

Lys Ile His Asn Tyr Ile Arg Ser Asp Arg Tyr Lys Pro Thr Leu Tyr
            85                  90                  95

Gln Glu Glu Lys Asn Gln Ile Val Glu Lys Asn Ser Lys Ala Tyr Thr
            100                 105                 110

Phe Lys Ala Glu Ser Ser Val Gly Gly Gln Pro Ala Asp Tyr Gln Arg
        115                 120                 125

Leu Pro Gln Glu Ser Ile Val Gln Ser Lys Leu Gly Gln Ser Gln Gly
    130                 135                 140

Ser Ser Ser Glu Asn Asp Cys Leu Lys Met Ile Tyr His Phe Tyr Glu
145                 150                 155                 160
```

```
Glu Asn Gly Phe Gly Thr Leu Ala Ser Lys Thr Ser Gln Asp Phe Lys
                165                 170                 175

Tyr Trp Leu Gln Asp Phe Ile Gln Lys Gly Ala Ser Gln Glu Glu Ala
        180                 185                 190

Cys Gln Leu Ile Leu His Ala Leu Gly Ile Ala Val Asp Arg Asn Lys
            195                 200                 205

Arg Asn Tyr Gly Tyr Val Asn Ala Ile Leu Lys Ser Trp Glu Gln Gln
        210                 215                 220

Asn Tyr Leu Ser Val His Glu Val Leu Val Asn Asp Lys Lys Gln Val
225                 230                 235                 240

Leu Glu His Ala Pro Gln Met Thr Glu Glu Tyr Gln Glu Leu Gly Phe
                245                 250                 255

<210> SEQ ID NO 6
<211> LENGTH: 280
<212> TYPE: PRT
<213> ORGANISM: Enterococcus faecalis

<400> SEQUENCE: 6

Met His Ala Thr Asp Gln Thr Phe Gln Ile Leu Leu Ser Gln Leu Leu
1               5                   10                  15

Glu Lys Val Glu Asp Arg Cys Pro Glu Cys Gly Ser Glu Gln Tyr Val
            20                  25                  30

Trp Gln Gln Lys Asn Lys Asp Gly Thr Glu Arg Cys Ala Pro Thr Cys
        35                  40                  45

Trp Ser Cys Gly Tyr Lys Met Leu Lys Lys His Glu Gln Gln Ala Asn
    50                  55                  60

Gln Gln Arg Ser Gln Glu Ser Phe Met Ala Arg Thr Gln Lys Phe Phe
65                  70                  75                  80

His Gln Gly Ser Leu Ile Ala Asp Asp Ala Leu Arg Gln Cys Arg Leu
                85                  90                  95

Thr Asn Tyr Gln Thr Thr Glu Leu Glu Thr Arg Gln Ala Lys Glu Arg
            100                 105                 110

Ala Leu Ala Ala Val Ser Ala Ile Val Glu Gly Lys Pro Ile His Val
        115                 120                 125

Ile Phe Ser Gly Lys Pro Gly Val Gly Lys Ser His Leu Ala Ile Ser
    130                 135                 140

Ile Leu Val Glu Val Leu Glu Arg Ser Ala Tyr Gln Lys Tyr Cys Leu
145                 150                 155                 160

Phe Val Ser Tyr Ser Glu Leu Leu Glu Lys Leu Lys Met Ser Met Asn
                165                 170                 175

Glu Ser Ala Lys Ser Gln Ala Lys Ala Gln Ala Tyr Ile Thr Arg Met
            180                 185                 190

Lys Lys Ala Asp Val Leu Val Leu Asp Asp Leu Gly Ala Glu Leu Gly
        195                 200                 205

Ile Lys Asn Lys Val Ser Thr Asp Phe Asn Asn Asp Ile Leu Asn Arg
    210                 215                 220

Ile Leu Glu Ala Arg Gln Asn Lys Ala Thr Ile Phe Thr Thr Asn Phe
225                 230                 235                 240

Ser Gly Lys Gln Leu Val Glu Ala Tyr Gly Thr Arg Ile Ile Ser Arg
                245                 250                 255

Leu Met Lys His Ala Asn Gly Tyr Val Phe Gln Tyr Lys Asp Thr Thr
            260                 265                 270

Asp Lys Arg Met Arg Ser Val Lys
        275                 280
```

<210> SEQ ID NO 7
<211> LENGTH: 123
<212> TYPE: PRT
<213> ORGANISM: Enterococcus faecalis

<400> SEQUENCE: 7

Met Ser Asn Leu Thr Lys Arg Lys Asp Leu Phe Glu Met Lys Ser
1               5                   10                  15

Val Val Phe Lys Asp Ile Ser Lys Gln Gln Ser Glu Lys Ala Gln Lys
                20                  25                  30

Arg Lys Arg Leu Leu Gln Leu Met Asn Gln Tyr Pro Asp Trp Ala Ser
            35                  40                  45

Gln Lys Asn Lys Leu Ile Met Gln Glu Ile Gln Glu Leu Gly Gln Ala
        50                  55                  60

Ile Gly Asn Trp Ser Met Asp Gln Ser Arg Pro Ile Gln Ser Ile Lys
65                  70                  75                  80

Ala Ala Ser Phe Thr Lys Ser Glu Tyr Leu Tyr Leu Ile Trp Leu Gly
                85                  90                  95

Tyr Ser Asp Glu Ala Ile Arg His Gly Leu Asp Met Ser Lys Glu Cys
            100                 105                 110

Tyr Phe Ile Tyr Arg Leu Thr Leu Leu Asn Glu
        115                 120

<210> SEQ ID NO 8
<211> LENGTH: 135
<212> TYPE: PRT
<213> ORGANISM: Enterococcus faecalis

<400> SEQUENCE: 8

Met Arg Thr Ser Thr Phe Asn Tyr Ile Lys Asp Ile Leu Ala Asp Phe
1               5                   10                  15

Tyr Lys Thr Glu Glu Tyr Ile Arg Gln Arg Glu Glu Leu Arg His
                20                  25                  30

Pro Tyr Gln Glu Ala Asp Leu Asn Ala Gly Ile Arg Gly Gln Gly Leu
            35                  40                  45

His Ser Val Val Thr Glu Arg Met Ala Ile Thr Ile Ala Met Asp Arg
        50                  55                  60

Arg Leu Trp Asn Leu Glu Arg Asn Arg Asp Ile Ile Lys Asn Cys Leu
65                  70                  75                  80

Ala Glu Ala Asp Glu Gln Thr Arg Val Ile Ile Glu Glu Leu Tyr Met
                85                  90                  95

Lys Lys Arg Pro Ser Leu Thr Leu Ile Gly Leu Ala Gln Gln Leu Phe
            100                 105                 110

Ile Ser Lys Ser Gln Ala Tyr Lys Leu Arg Asn His Phe Phe Glu Ala
        115                 120                 125

Val Ala Asp Glu Leu Gly Met
    130                 135

<210> SEQ ID NO 9
<211> LENGTH: 130
<212> TYPE: PRT
<213> ORGANISM: Enterococcus faecalis

<400> SEQUENCE: 9

Met Asn Glu Ala Glu Gln Glu Leu Tyr Glu Ala Leu Val Ala Ile Cys
1               5                   10                  15

```
Gln Thr Ser Gly Phe Leu Leu Glu Leu Pro Thr Asp Leu Pro
            20                  25                  30

Asp Gln Pro Phe Val Tyr Leu Gly Asp Ser Lys Glu Leu Pro Lys Pro
        35                  40                  45

Thr Lys Ser Ala Ile Leu Gly Glu Ile Glu Leu Ile Met His Val Tyr
 50                  55                  60

Gly Ala Leu Ser Glu Arg Gln Gln Ile Ser Thr Ile Lys Gly Thr Ile
 65                  70                  75                  80

Leu Arg Gln Ala Thr Ser Asn Leu Lys Arg Thr Ala His Phe Asn Trp
                85                  90                  95

Gly Ile Lys His Gln Glu Val Lys Ala Gln Met Val Lys Asp Thr Lys
               100                 105                 110

Gln Met Lys Lys Thr Ile Trp His Ala Val Leu Pro Leu His Met Gln
           115                 120                 125

Phe Tyr
   130

<210> SEQ ID NO 10
<211> LENGTH: 170
<212> TYPE: PRT
<213> ORGANISM: Enterococcus faecalis

<400> SEQUENCE: 10

Met Gly Glu Val Met Gln Gly Lys Asp Arg Ile Leu Leu Val Arg Arg
 1               5                  10                  15

Leu Asp Glu Ala Ala Thr Lys Lys Ala Met Lys Pro Leu Phe Gln Ile
                20                  25                  30

Glu His Glu Trp Glu Phe Ser Arg Glu Ser Ser Gly Thr Gln Thr Lys
            35                  40                  45

Asp Gly Val Ala Asn Ala Val Ser Gly Leu Glu Val Thr Leu Ser Leu
 50                  55                  60

Ser Gly Leu Ala Ser Arg Asp Asp Glu Asn Leu Tyr Met Lys Asp Ala
 65                  70                  75                  80

Val Glu Asp Gly Ile Leu Met Glu Phe Trp Asp Val Asp Leu Lys Gly
                85                  90                  95

Glu Lys Asn Ala Glu Gly Lys Tyr Pro Ala Ile Tyr Ala Gln Gly Tyr
               100                 105                 110

Val Asn Ser Trp Ser Leu Pro Ala Asn Val Glu Glu Leu Val Glu Ile
           115                 120                 125

Glu Thr Glu Ala Ser Ile Asn Gly Lys Pro Gln Asp Gly Phe Ala Thr
       130                 135                 140

Val Glu Ala Asp Ile Ile Ala Glu Ala Gln Tyr Ala Phe Gln Asp Thr
145                 150                 155                 160

Val Pro Asp Lys Ala Pro Gln Pro Gly Glu
                165                 170

<210> SEQ ID NO 11
<211> LENGTH: 119
<212> TYPE: PRT
<213> ORGANISM: Enterococcus faecalis

<400> SEQUENCE: 11

Met Asn Leu Glu Ile Asn Gly Lys Thr Ile Glu Val Lys Phe Thr Ile
 1               5                  10                  15

Gly Ala Ile Arg Glu Leu Asp Lys Arg Tyr Gln Ile Glu Asn Gly Ala
                20                  25                  30
```

```
Ala Lys Phe Gly Met Gly Ile Ser Ala Met Ile Tyr Leu Arg Gln
            35                  40                  45

Tyr Asn Pro Val Ile Leu Val Asp Ile Met Glu Ala Leu Gln Ser Gly
 50                  55                  60

Gln Leu Lys Ile Gly Lys Ser Glu Ile Glu Ala Trp Leu Met Thr Gln
 65                  70                  75                  80

Asp Val Lys Lys Leu Ser Asp Leu Leu Lys Glu Met Gly Lys Gln
                    85                  90                  95

Pro Leu Thr Lys Pro Met Ile Asp Gln Phe Ser Lys Glu Ala Lys Lys
                100                 105                 110

Ala Glu Ala Gln Ala Thr Asn
            115

<210> SEQ ID NO 12
<211> LENGTH: 122
<212> TYPE: PRT
<213> ORGANISM: Enterococcus faecalis

<400> SEQUENCE: 12

Met Tyr His Asp Ile Ala Leu Ser Ala Phe Arg Tyr Leu Gly Cys Arg
 1               5                  10                  15

Ser Phe Glu Glu Val Asp Gln Met Thr Met Ser Glu Phe Glu Leu Arg
                20                  25                  30

Met Ile Ala Phe Asn Leu Ala Glu Val Asp Glu Glu Arg Lys Arg His
            35                  40                  45

Glu Leu Ala Tyr Leu Asn Val Lys Ala Gln Ala Thr Asn Lys Lys Gly
 50                  55                  60

Lys Pro Val Phe Glu Ser Phe Lys Ser Phe Tyr Asp Tyr Glu Lys Arg
 65                  70                  75                  80

Val Ala Glu Val Leu Ala Ala Asn Gln Pro Gln Arg Thr Lys Leu Asn
                    85                  90                  95

Glu Arg Lys Lys Thr Gln Leu Ala Thr Val Ala Glu Arg Leu Arg Arg
                100                 105                 110

Tyr Arg Glu Gly Arg Arg Val Asp Gly Glu
            115                 120

<210> SEQ ID NO 13
<211> LENGTH: 977
<212> TYPE: PRT
<213> ORGANISM: Enterococcus faecalis

<400> SEQUENCE: 13

Met Glu Asn Asp Lys Glu Lys Thr Pro Leu Ser Glu Ala Lys Lys Ser
 1               5                  10                  15

Leu Ala Gly Val Gln Gln Ala Leu Lys Ser Met Ser Gly Glu Tyr Ala
                20                  25                  30

Leu Leu Ser Gly Tyr Leu Gly Lys Ile Ser Ala Gly Val Asn Gln Ser
            35                  40                  45

Ala Thr Val Met Asn Thr Phe Lys Thr Val Met Gln Gln Ser Gly Glu
 50                  55                  60

Thr Val Lys Lys Thr Gly Asp Glu Thr Ala Lys Ala Ala Asp Gln Met
 65                  70                  75                  80

Asn Thr Ala Leu Thr Asp Ser Ala Glu Gln Ala Gly Glu Ala Ala Lys
                    85                  90                  95

Lys Ala Gly Lys Glu Thr Ser Asp Gly Phe Thr Asn Ala Gln Asn Asn
                100                 105                 110
```

```
Met Leu Ser Phe Gly Thr Ala Met Thr Ser Ala Val Ser Leu Pro Met
            115                 120                 125

Leu Asn Val Leu Lys Thr Ala Met Gly Val Gly Ala Gly Val Ser Gly
        130                 135                 140

Glu Phe Gln Gly Met Gln Gly Leu Ile Met Ala Ser Ala Gly Gly Ile
145                 150                 155                 160

Ser Asp Ser Leu Gln Gly Glu Leu Gln Gly Ala Leu Thr Gln Met Asn
                165                 170                 175

Gln Ser Phe Glu Ala Ala Ala Gln Val Ile Gln Ser Val Met Ala Pro
            180                 185                 190

Gly Met Glu Ile Leu Val Gln Val Val Ile Thr Val Val Lys Gly Ile
            195                 200                 205

Thr Ala Leu Val Asn Leu Phe Ile Lys Leu Pro Lys Pro Val Gln Val
210                 215                 220

Phe Ile Val Ala Ile Met Gly Ile Leu Ala Ala Ile Gly Pro Met Leu
225                 230                 235                 240

Ile Met Val Thr Met Ala Gln Leu Lys Phe Gln Gln Phe Ser Ala Gly
                245                 250                 255

Leu Ala Leu Val Gln Gly Asn Ile Gly Lys Leu Gly Gly Gly Leu Ser
            260                 265                 270

Lys Leu Ser Ala Ser Phe Ser Ala Leu Gly Gly Pro Leu Ile Leu
275                 280                 285

Ile Val Ala Ala Val Leu Ala Ala Val Ala Ala Phe Ile Tyr Phe Tyr
            290                 295                 300

Lys Thr Asn Glu Thr Phe Arg Asn Ser Ile Asn Ser Leu Ala Ser Ala
305                 310                 315                 320

Ile Gln Gly Ala Val Ser Ala Ala Phe Gly Lys Leu Val Gly Leu Leu
                325                 330                 335

Gln Gln Ile Gln Pro Ala Phe Gln Gln Val Met Ala Val Phe Lys Gln
            340                 345                 350

Phe Phe Ala Val Gly Leu Glu Lys Met Ala Thr Ile Phe Ser Thr Ile
            355                 360                 365

Gly Arg Val Leu Ala Gly Val Phe Ala Ser Gly Leu Gln Leu Gly Ser
370                 375                 380

Asn Leu Leu Gly Gln Phe Gly Thr Phe Asp Lys Ala Gly Leu Ala
385                 390                 395                 400

Val Gly Leu Leu Val Lys Val Leu Thr Lys Val Ala Leu Ala Ala Leu
                405                 410                 415

Gly Ile Ser Gly Pro Phe Gly Leu Ile Ile Ser Leu Ile Val Ser Phe
            420                 425                 430

Val Thr Ala Trp Met Lys Thr Gly Asp Leu Ser Ala Gly Gly Ile Thr
            435                 440                 445

Gln Val Phe Asp Asn Leu Gly Asn Thr Ile Thr Ser Val Thr Thr Met
            450                 455                 460

Leu Ala Thr Asn Leu Pro Lys Val Ile Gln Leu Phe Thr Thr Val Leu
465                 470                 475                 480

Thr Ser Ile Leu Gly Lys Ile Thr Glu Ala Ile Pro Ser Ile Val Thr
                485                 490                 495

Ala Leu Ser Ser Leu Ile Thr Leu Ile Val Gly Ala Ile Val Ala Asn
            500                 505                 510

Leu Pro Val Leu Ile Glu Ala Thr Gln Ile Thr Thr Leu Ile
            515                 520                 525

Gln Gly Ile Thr Thr Val Leu Pro Met Leu Ile Glu Val Gly Leu Ser
```

```
                530             535             540
Leu Leu Met Thr Leu Val Asn Ala Ile Val Thr Ala Leu Pro Thr Ile
545                 550             555             560

Thr Thr Ala Ala Ile Asn Ile Ile Thr Thr Leu Val Thr Ala Phe Val
                565             570             575

Thr Ala Leu Pro Met Leu Val Thr Ala Gly Val Ser Ile Ile Thr Ala
            580             585             590

Leu Val Asn Ala Phe Val Thr Met Leu Pro Leu Ile Leu Thr Ala Gly
        595             600             605

Leu Gln Ile Leu Met Ala Leu Ile Thr Gly Ile Met Thr Ile Leu Pro
    610             615             620

Gln Leu Ile Gln Ser Ala Leu Thr Ile Ile Leu Ala Leu Val Thr Ala
625             630             635             640

Leu Ile Gly Ala Leu Pro Gln Ile Ile Ser Ala Gly Val Lys Leu Leu
            645             650             655

Met Ala Leu Ile Gln Gly Ile Ile Ser Ile Leu Pro Thr Leu Val Ala
            660             665             670

Ala Ala Ile Thr Leu Ile Leu Thr Leu Val Asn Ala Leu Ile Gly Ala
            675             680             685

Leu Pro Gln Ile Ile Ser Ala Gly Val Lys Leu Leu Met Ala Leu Ile
    690             695             700

Gln Gly Ile Ile Ser Ile Leu Pro Gln Leu Val Thr Ala Ala Ile Thr
705             710             715             720

Leu Ile Thr Ala Leu Met Gly Ala Leu Ile Asn Ala Leu Pro Gln Leu
            725             730             735

Leu Ser Ala Gly Ile Gln Leu Ile Gln Ala Leu Ile Asn Gly Val Leu
            740             745             750

Ser Leu Leu Gly Ala Leu Leu Ser Ala Ala Gly Thr Leu Ile Ser Gln
            755             760             765

Met Ile Thr Lys Ile Gly Ser Tyr Phe Gly Gln Leu Leu Ala Ser Gly
            770             775             780

Gly Gln Leu Val Glu Asn Ile Lys Asn Gly Val Thr Asn Ala Ala Asn
785             790             795             800

Gln Val Lys Asn Ala Ile Gly Ser Val Ile Glu Gly Ala Trp Gln Ala
                805             810             815

Ile Gln Gly Trp Phe Ser Lys Phe Thr Asp Ala Gly Ala Asn Ile Val
            820             825             830

Gly Met Ile Ala Asp Gly Ile Thr Gly Ala Ile Gly Lys Ala Lys Glu
            835             840             845

Ala Ile Asp Gly Val Val Ser Lys Ile Arg Asn Phe Leu Pro Phe Ser
850             855             860

Pro Ala Lys Glu Gly Pro Leu Ser Asp Leu His Lys Leu Asn Phe Gly
865             870             875             880

Gly Thr Ile Ala Thr Gly Ile Tyr Ala Gly Glu Thr Ala Val Ser Arg
            885             890             895

Ala Met Ala Ser Ile Leu Asp Leu Pro Leu Leu Asn Asp Phe Ala Leu
            900             905             910

Asp Leu Ala Gly Arg Gly Asn Phe Thr Ala Thr Ile Asp His Arg Leu
            915             920             925

Glu Asn Asp Ala Tyr Asn Arg Pro Leu Phe Val Thr Val Glu Ser Thr
930             935             940

Leu Asp Gly Lys Val Val Ala Ala Thr Thr Ala Pro Tyr Leu Ala Thr
945             950             955             960
```

Glu Leu Gln Arg Gln Gln Val Lys Gln Asn Asn Arg Leu Gly Arg Arg
            965                 970                 975

Gly

<210> SEQ ID NO 14
<211> LENGTH: 308
<212> TYPE: PRT
<213> ORGANISM: Enterococcus faecalis

<400> SEQUENCE: 14

Met Tyr Lys Phe Val Asp Thr Asn Gln Ala Thr His Ser Thr Pro Leu
1               5                   10                  15

Pro Ser Glu Ala Leu Asn Phe Asn Gly Gln Phe Leu Glu Lys Val Ile
            20                  25                  30

Pro Gly Tyr Gln Thr Leu Ser Val Ser Gly Arg Glu Leu Val Pro Ser
        35                  40                  45

Glu Ile Glu Ser Tyr Gln Leu Gly Ile Arg Asp Gly Lys Arg His Val
    50                  55                  60

Tyr Ala Arg Ile Pro Glu Arg Glu Leu Thr Val Lys Tyr Arg Leu Ser
65                  70                  75                  80

Ala Val Asn Asn Glu Ala Phe Arg Asp Ala Phe Asn His Leu Asn Val
                85                  90                  95

Ala Leu Phe Thr Glu Lys Asp Val Ser Ile Trp Phe Asn Asp Glu Pro
            100                 105                 110

Glu Met Leu Trp Phe Gly Ser Lys Ser Ser Val Ser Asp Val Pro Glu
        115                 120                 125

Gly Val Asn Gln Val Thr Gly Thr Phe Thr Leu Leu Leu Ser Asp Pro
    130                 135                 140

Tyr Lys Tyr Thr Arg Ser Asp Ala Thr Ser Val Met Trp Gly Ser Pro
145                 150                 155                 160

Thr Ile Thr Phe Gln Ala Asn Tyr Leu Met Gly Asn Thr Gly Ser Gly
                165                 170                 175

Ala Phe Asp Phe Pro Ile Leu Ile Glu Gly Gly Ala Tyr Trp Gly Ser
            180                 185                 190

Thr Met Ile Thr Phe Gln Asn Arg Ala Tyr Thr Met Gly Asp Leu Gly
        195                 200                 205

Lys Glu Val Arg Pro Ile Glu Ile Tyr Pro Thr Val Glu Gly Leu Lys
    210                 215                 220

Val Lys Pro Thr Ile Ile Leu Thr Gly Thr Gly Arg Gly Val Trp Ile
225                 230                 235                 240

Lys Thr Arg Asn Asp Thr Ile Asn Leu Gly Asp Phe Asp Arg Ser Glu
                245                 250                 255

Ile Ile Ile Asp Thr Glu Asn Phe Tyr Leu Thr Lys Asn Gly Ala Pro
            260                 265                 270

Met Ile Arg Pro Met Asn Asp Phe Tyr Leu Tyr Pro Asn Glu Pro Leu
        275                 280                 285

Tyr Ile Gln Ala Lys Asp Ser Asp Phe Arg Leu Thr Ile Arg Tyr Pro
    290                 295                 300

Asn Arg Phe Val
305

<210> SEQ ID NO 15
<211> LENGTH: 485
<212> TYPE: PRT
<213> ORGANISM: Enterococcus faecalis

<400> SEQUENCE: 15

```
Met Leu Met Ala Leu Asp Leu Lys Arg Thr Tyr Thr Ala Ile Leu Asp
1               5                   10                  15

Asn Ala Tyr Gln Val Ser Tyr Glu Lys Ile Glu Asn Lys Ile Gly Ser
            20                  25                  30

Leu Asp Phe Thr Met Pro Leu Asp Pro Lys Asn Glu Phe Ile Ala
        35                  40                  45

Glu Met Gln Trp Val Glu Leu Thr Asp Asn Glu Asn Glu Tyr Ile Gly
    50                  55                  60

Leu Tyr Arg Val Met Pro Thr Thr Ile Lys Lys Asp Ala Asn Asn Asn
65              70                  75                      80

Gln Ile His Tyr Ser Ala Thr Glu Ala Leu Cys Thr Leu Gly Asp Thr
                85                  90                  95

Val Leu Phe Gly Cys His Glu Ile Lys Asn Lys Thr Thr Lys Glu Ala
                100                 105                 110

Ile Gln Phe Leu Leu Asn Lys Gln Lys Thr Lys His Trp Val Leu Lys
                115                 120                 125

Lys Cys Asp Phe Ser Arg Lys Leu Thr Tyr Lys Trp Glu Asn Glu Asn
    130                 135                 140

Gly Leu Val Glu Pro Leu Phe Ser Ile Pro Ala Asp Phe Glu Glu Glu
145                 150                 155                 160

Tyr Leu Trp Gln Trp Asn Thr Glu Val Tyr Pro Phe Glu Leu Ser Leu
                165                 170                 175

Val Lys Pro Pro Thr Glu Pro Val Ala Arg Ile Gln Glu Gly Tyr Asn
                180                 185                 190

Met Gln Gly Phe Glu Ile Glu Arg Asn Pro Lys Met Leu Ile Asn Arg
                195                 200                 205

Ile Tyr Pro Leu Gly Ser Gly Glu Gly Val Asn Lys Val Asn Ile Arg
210                 215                 220

Ser Val Asn Gln Gly Val Pro Tyr Leu Glu Asn Lys Ala Ala Ile Asp
225                 230                 235                 240

Arg Tyr Gly Leu Leu Glu Ser Ile Trp Val Glu Gln Arg Phe Ser Asp
                245                 250                 255

Pro Lys Ala Leu Lys Glu Asn Ala Leu Arg Met Leu Glu Glu Trp Thr
            260                 265                 270

Lys Pro Gln Val Ser Trp Val Val Thr Ala Ala Asp Leu Ile Lys Leu
            275                 280                 285

Thr Asp Gln Pro Leu Ala Ile Asp Arg Leu Arg Leu Gly Thr Val Ile
        290                 295                 300

Met Ile Asn Thr Asn Glu Phe Gly Ser Val Asn Leu Arg Ile Lys Lys
305                 310                 315                 320

Glu Ser Lys Lys Asp Val Phe Gly Ala Pro Gln Asp Ile Gln Leu Glu
                325                 330                 335

Leu Gly Asn Leu Gln Glu Thr Ile His Ser Thr Met Thr Ala Phe Ser
            340                 345                 350

Arg Lys Gln Glu Ile Asn Glu Thr Tyr Ala Gln Gly Ala Thr Thr Leu
        355                 360                 365

Leu Asn Arg Ser Ile Gln Gly Glu Leu Ser Lys Thr Gln Pro Val Glu
        370                 375                 380

Leu Asn Leu Tyr Phe Asp Glu Asp Ile Leu Tyr Ile Asn Thr Ala Glu
385                 390                 395                 400

Leu Thr Phe Lys Ala Thr Ala Lys Gly Pro Ser His Ser Val Thr Asn
```

```
            405                 410                 415
Ile Asp Leu Val Val Asp Gly Lys Lys Leu Pro Gln Leu Ser Leu Gln
                420                 425                 430

Gln Gln Arg Leu Asn Ile Leu Ser Tyr Leu Arg Lys Thr Thr Asp Glu
            435                 440                 445

Lys Ile Glu Arg Gly Asn His Thr Leu Gln Phe Phe Ser His Gln Pro
    450                 455                 460

Leu Trp Leu Asp Ala Ser Val Ile Cys Arg Val Tyr Ile Gln Ser Gln
465                 470                 475                 480

Leu Gly Gly Gln Phe
            485

<210> SEQ ID NO 16
<211> LENGTH: 589
<212> TYPE: PRT
<213> ORGANISM: Enterococcus faecalis

<400> SEQUENCE: 16

Met Ser Val Glu His Ile Glu Glu Leu Asp Thr Leu Asn Gln Gly Arg
1               5                   10                  15

Leu Lys Ile Asn Ala Ile Leu Asp Gln Ser Asn Ala Ser Ala Glu Lys
            20                  25                  30

Val Asp Ala Tyr Gln Val Gln Leu Thr Asn Gly Ile Ser Glu Ala Lys
        35                  40                  45

Asn Ile Ala Asp Glu Ala Gly Lys Glu Ala Val Gln Ile Ala Thr Asp
    50                  55                  60

Ala Gly Asn Gln Ala Asn Glu Thr Ala Asn Gln Ala Met Asn Asn Ala
65                  70                  75                  80

Lys Thr Ala Ile Met Ile Ala Gly Asn Ala Val Ser Thr Ala Asn Asn
                85                  90                  95

Asn Lys Gln Glu Phe Asp Thr Leu Arg Asn Asp Phe Asp Gln Leu Val
            100                 105                 110

Ala Glu Ala Gly Asp Ser Asn Pro Glu Ile Val Gln Ala Arg Thr Asp
        115                 120                 125

Thr Gln Gly Ile Lys Gln Ala Thr Leu Ala Asn Arg Leu Gln Ile Asp
    130                 135                 140

Leu Asn Asp Arg Met Thr Lys Ala Asp Gly Ile Ser Leu Leu Ala Lys
145                 150                 155                 160

Pro Thr Thr Val Lys Met Lys Leu Asp Phe Asn Gly Lys Thr Ala Gly
                165                 170                 175

Asn Thr Ala Thr Asn Ala Asn Ser Tyr Ser Thr Asp Phe Thr Ala Lys
            180                 185                 190

Ile Leu Lys Lys Pro Thr Glu Val Trp Glu Glu Val Ser Gln Ala Asp
        195                 200                 205

Tyr Asn Lys Met Ala Ser Arg Asp Asp Glu Gly Val Lys Thr Gly Ser
    210                 215                 220

Thr Gln Ser Gly Val Ile Pro Gln Gln Leu Ala Ala Phe Asn Leu Val
225                 230                 235                 240

Glu Ala Ala Lys Lys Leu Ile Pro Gln Met Phe Glu Thr Val Thr Thr
                245                 250                 255

Asp Glu Ala Val Ala Phe Ile Arg Gln Asn Val Gln Phe Phe Thr Ile
            260                 265                 270

Asn Gln Arg Val Lys Ala Ala Pro Asn Asn Gln Thr Ile Lys Ile
        275                 280                 285
```

```
Ala Thr Tyr Leu Pro Thr Thr Asp Asn Trp Val Thr Gln Ile Gln Glu
    290                 295                 300

Ser Ala Lys Glu Phe Gly Asp Phe Ser Ile Gln Ile Asn Asp Gln Asn
305                 310                 315                 320

Phe Ile Thr Asp Glu Gly Phe Ile Tyr Leu Met Ser Tyr Thr Asp Ser
                325                 330                 335

Ser Asn Gly Val Thr Pro Ala Ser Leu Glu Val Asp Tyr Val Gly Leu
            340                 345                 350

His Ile Gly Leu Ser Val Asp Ala Gln Ala Val Leu Ala Lys Ser Gly
        355                 360                 365

Phe Val Gln Ala Glu Gln Leu Asn Thr His Met Glu Asn Gln Asp Asn
370                 375                 380

Pro His Gln Val Thr Ala Glu Gln Val Gly Leu Gly Asn Val Glu Asn
385                 390                 395                 400

Tyr Gly Phe Ala Ser Asp Ser Glu Ala Val Ala Gly Thr Leu Thr Ser
                405                 410                 415

Lys Tyr Met His Pro Lys Asn Val Ala Glu Ala Ile Lys Gly Gln Ala
            420                 425                 430

Val Thr Gln Thr Gly Asp Gln Glu Ile Ala Gly Val Lys Asn Phe Val
        435                 440                 445

Thr Met Pro Thr Val Asn Gly Val Pro Leu Glu Ser Ser Arg Met Ala
450                 455                 460

Ile Tyr Glu Ala Ser Gly Val Gly Glu Val Glu Ala Lys Tyr Gln Ala
465                 470                 475                 480

Ala Phe Asn Lys Asp Asn Met Lys Phe Val Leu Ile Arg Val Gly Asn
                485                 490                 495

Arg Val Asp Ala Phe Val Arg Cys Asn Leu Ser Asp Pro Thr Lys Leu
            500                 505                 510

Asn Asn Asn Leu Val Lys Val Phe Thr Val Pro Thr Gly Tyr Thr Leu
        515                 520                 525

Ser Thr Lys Ile Thr Lys Gly Ile Trp Asn Leu Ala Leu Thr Ala Met
    530                 535                 540

Gln Tyr Thr Phe Pro Gln Pro Asn Cys Ala Gly Leu Tyr Glu Met Gly
545                 550                 555                 560

Asn Gln Gly Ile Leu Phe Gly Ala Asn Arg Ala Gly Asn Ile Tyr Leu
                565                 570                 575

Gln Gly Ser Trp Tyr Thr Asp Asp Pro Phe Pro Thr Lys
            580                 585

<210> SEQ ID NO 17
<211> LENGTH: 131
<212> TYPE: PRT
<213> ORGANISM: Enterococcus faecalis

<400> SEQUENCE: 17

Met Glu Arg Tyr Leu Asn Thr Ile Thr Met Leu Leu Ser Ile Phe Gly
1               5                   10                  15

Gly Ile Val Val Arg Leu Leu Gly Gly Leu Asp Gln Leu Leu Asp Val
            20                  25                  30

Phe Leu Phe Leu Ile Ile Val Asp Phe Ile Thr Gly Trp Ile Lys Ala
        35                  40                  45

Ile Ala Thr Lys Glu Leu Ser Ser Arg Ile Gly Met Leu Gly Ile Ala
    50                  55                  60

Lys Lys Val Thr Met Leu Phe Val Val Ala Val Ala Val Arg Val Glu
65                  70                  75                  80
```

```
Lys Val Val Gly Asn Asn Leu Pro Ile Arg Glu Met Val Leu Ile Phe
                85                  90                  95

Tyr Ile Ala Asn Glu Gly Leu Ser Phe Phe Glu Asn Ile Ala Thr Phe
                100                 105                 110

Ile Pro Met Pro Lys Lys Leu Lys Glu Leu Phe Ile Gln Leu Lys Asn
                115                 120                 125

Lys Asp Asp
        130

<210> SEQ ID NO 18
<211> LENGTH: 365
<212> TYPE: PRT
<213> ORGANISM: Enterococcus faecalis

<400> SEQUENCE: 18

Met Phe Lys Lys Leu Met Ile Gln Leu Ala Leu Val Ile Gly Leu Ser
1               5                   10                  15

Leu Thr Ile Pro Met Thr Ala Cys Ala Tyr Thr Ile Glu Ala Asp Pro
                20                  25                  30

Ile Asn Phe Thr Tyr Phe Pro Gly Ser Ala Ser Asn Glu Leu Ile Val
                35                  40                  45

Leu His Glu Ser Gly Asn Glu Arg Asn Leu Gly Pro His Ser Leu Asp
        50                  55                  60

Asn Glu Val Ala Tyr Met Lys Arg Asn Trp Ser Asn Ala Tyr Val Ser
65                  70                  75                  80

Tyr Phe Val Gly Ser Gly Gly Arg Val Lys Gln Leu Ala Pro Ala Gly
                85                  90                  95

Gln Ile Gln Tyr Gly Ala Gly Ser Leu Ala Asn Gln Lys Ala Tyr Ala
                100                 105                 110

Gln Ile Glu Leu Ala Arg Thr Asn Asn Ala Ala Thr Phe Lys Lys Asp
                115                 120                 125

Tyr Ala Ala Tyr Val Asn Leu Ala Arg Asp Leu Ala Gln Asn Ile Gly
        130                 135                 140

Ala Asp Phe Ser Leu Asp Asp Gly Thr Gly Tyr Gly Ile Val Thr His
145                 150                 155                 160

Asp Trp Ile Thr Lys Asn Trp Trp Gly Asp His Thr Asp Pro Tyr Gly
                165                 170                 175

Tyr Leu Ala Arg Trp Gly Ile Ser Lys Ala Gln Leu Ala Gln Asp Leu
                180                 185                 190

Gln Thr Gly Val Ser Glu Thr Gly Glu Thr Val Ile Ile Gln Pro Gly
                195                 200                 205

Lys Pro Asn Ala Pro Lys Tyr Gln Val Gly Gln Ala Ile Arg Phe Thr
        210                 215                 220

Ser Ile Tyr Pro Thr Pro Asp Ala Leu Ile Asn Glu His Leu Ser Ala
225                 230                 235                 240

Glu Ala Leu Trp Thr Gln Val Gly Thr Ile Thr Ala Lys Leu Pro Asp
                245                 250                 255

Arg Gln Asn Leu Tyr Arg Val Glu Asn Ser Gly His Leu Leu Gly Tyr
                260                 265                 270

Val Asn Asp Gly Asp Ile Ala Glu Leu Trp Arg Pro Gln Thr Lys Lys
        275                 280                 285

Ser Phe Leu Ile Gly Val Asp Glu Gly Ile Val Leu Arg Ala Gly Gln
                290                 295                 300

Pro Ser Leu Leu Ala Pro Ile Tyr Gly Ile Trp Pro Lys Asn Thr Arg
```

```
305                 310                 315                 320
Phe Tyr Tyr Asp Thr Phe Tyr Ile Ala Asp Gly Tyr Val Phe Ile Gly
                325                 330                 335

Gly Thr Asp Thr Thr Gly Ala Arg Ile Tyr Leu Pro Ile Gly Pro Asn
            340                 345                 350

Asp Gly Asn Ala Gln Asn Thr Trp Gly Ser Phe Ala Ser
        355                 360                 365

<210> SEQ ID NO 19
<211> LENGTH: 689
<212> TYPE: PRT
<213> ORGANISM: Enterococcus faecium

<400> SEQUENCE: 19

Met Leu Met Thr Met Asn Leu Ser Arg Glu Tyr Thr Ala Ile Leu Glu
1               5                   10                  15

Asn Ala Tyr Asp Val Ser Tyr Glu Lys Ile Glu Asn Glu Ile Gly Ser
            20                  25                  30

Ile Glu Phe Thr Met Pro Leu Tyr Asp Thr Lys Asn Ser Met Ile Gln
        35                  40                  45

Ala Leu Gln Tyr Val Glu Leu Thr Asp Asn Glu Asn Gly Tyr Ile Gly
    50                  55                  60

Leu Tyr Arg Ile Met Pro Ser Thr Ile Gln Lys Asp Pro Ser Asn Tyr
65                  70                  75                  80

Ser Ile Lys Tyr Thr Ala Ile His Val Ile Gly Thr Leu Leu Asp Ser
                85                  90                  95

Val Leu Phe Gly Tyr His Glu Leu Val Asn Arg Thr Thr Thr Asp Val
            100                 105                 110

Ile Asn Tyr Val Leu Asn Gln Gln Lys Lys Lys His Trp Val Leu Lys
        115                 120                 125

Lys Cys Glu Phe Thr Arg Tyr Phe Ser Tyr Ala Trp Glu Asn Glu Asn
    130                 135                 140

Gly Leu Ala Asp Ala Leu Phe Ser Ile Pro Lys Ala Phe Asp Glu Asp
145                 150                 155                 160

Tyr Met Trp Ser Trp Asn Thr Gln Val Tyr Pro Phe Glu Leu Ser Leu
                165                 170                 175

Val Lys Pro Pro Thr Glu Pro Val Cys Arg Ile Gln Glu Gly Tyr Asn
            180                 185                 190

Met Glu Gly Phe Glu Ile Glu Thr Asp Pro Asn Asn Leu Val Asn Arg
        195                 200                 205

Val Tyr Pro Leu Gly Ala Gly Glu Gly Val Asn Gln Leu Asn Ile Lys
    210                 215                 220

Ser Val Asn Asn Asn Val Pro Tyr Val Glu Asp Ala Glu Ser Ile Lys
225                 230                 235                 240

Lys Tyr Gly Leu Ile Glu Tyr Val Trp Val Asp Gln Arg Phe Thr Ile
                245                 250                 255

Ala Gln Ala Leu Lys Asp Asn Ala Ile Ser Met Leu Lys Lys Trp Ser
            260                 265                 270

Ile Pro Lys Val Ser Trp Lys Val Ser Ala Ala Asp Leu Ile Lys Leu
        275                 280                 285

Thr Asp Thr Pro Leu Glu Ile Asp Lys Leu Arg Gln Gly Thr Val Val
    290                 295                 300

Met Ile Asn Thr Asn Glu Tyr Gly Ser Phe Asn Leu Arg Ile Lys Lys
305                 310                 315                 320
```

```
Glu Ser Lys Ser Asp Val Phe Gly Ala Pro Gln Ser Ile Gln Leu Glu
            325                 330                 335

Leu Gly Asn Leu Lys Asp Asp Ile Ser Thr Thr Met Ser Asp Leu Asn
        340                 345                 350

Arg Lys Gln Gln Ile Asn Glu Thr Tyr Ser Gln Gly Ala Thr Asn Ile
        355                 360                 365

Leu Asn Tyr Ser Tyr Gln Asp Asn Cys Glu Ser Ala Tyr Pro Ala Glu
370                 375                 380

Ile Glu Phe Tyr Leu Asp Asp Val Phe His Val Asn Thr Val Glu
385                 390                 395                 400

Leu Thr Phe Lys Thr Lys Arg Tyr Arg Gly Tyr Thr Lys Ala Val Lys
                405                 410                 415

Gly Gly Gly Ala Lys Thr Ile Thr Ser Glu Ala Gly Gly Gln Ser Thr
                420                 425                 430

Gln Thr Ser Ser Ala Gly Gly Ser Arg Gln Thr Ser Ser Ala Gly
            435                 440                 445

Gly Gly Ser Val Gln Ser Thr Thr Ala Gly Gly Gly Val Thr Thr
        450                 455                 460

Ser Gly Ser Gly Gly Gly Ser Tyr Gln Gly Ser Ser Thr Ser Val Gly
465                 470                 475                 480

Gly Gly Ser Thr Gln Thr Ser Ser Ala Asn Gly Thr His Arg His Met
                485                 490                 495

Met Phe Glu Ser Val Asp Ala Ser Gly Pro Ile Gln Thr Thr Arg Tyr
                500                 505                 510

Lys Ala Tyr Gly Ser Ser Leu Met Gln Met Gln Gly Ser Pro Gly Lys
                515                 520                 525

Ile Tyr Thr Ala Glu Ala Ala Asp Asn His Thr His Thr Val Asn Ile
            530                 535                 540

Pro Asn His Ser His Asn Phe Thr Ile Asn Val Pro Ala His Thr His
545                 550                 555                 560

Asn Val Ser Ile Pro Ser His Ala His Ser Val Asn Ile Pro Asn His
                565                 570                 575

Thr His Ser Val Asn Ile Pro Asn His Thr His Thr Val Lys Ile Pro
            580                 585                 590

Ser His Lys His Asn Val Val Leu Pro Glu His Thr His Pro Leu Glu
        595                 600                 605

Trp Gly Ile Phe Gln Ala Ser Asp Ser Pro Ser Val Asp Ile Val
        610                 615                 620

Val Asp Gly Lys Thr Ile Pro His His Glu Thr Ser Gln Asn Arg Leu
625                 630                 635                 640

Asn Leu Val Asp Tyr Leu Lys Lys Thr Ser Ser Gly Gln Ile Gln Arg
                645                 650                 655

Gly Ser His Thr Ile Gln Ile Lys Pro Asn Lys Leu Ala Arg Ile Glu
            660                 665                 670

Ala Gln Val Thr Cys Arg Val Phe Ile Gln Ser Gln Leu Gly Gly Gln
        675                 680                 685

Phe

<210> SEQ ID NO 20
<211> LENGTH: 59
<212> TYPE: PRT
<213> ORGANISM: Enterococcus faecium

<400> SEQUENCE: 20
```

```
Met Leu Val Lys Val Lys Lys Ile Asn Gly Glu Glu Phe Ile Ala Glu
1               5                   10                  15

Val Asn Gln Thr Ile Gln Glu Ile Tyr Asp Glu Leu Ser Asn Asn Leu
            20                  25                  30

Asp Gly Ser Phe Ile Leu Phe Gly Glu Arg Ile Glu Gln Lys Met Thr
                35                  40                  45

Ile Glu Ser Val Tyr Lys Asp Lys Val Gly Ala
50                  55
```

<210> SEQ ID NO 21
<211> LENGTH: 649
<212> TYPE: PRT
<213> ORGANISM: Enterococcus faecium

<400> SEQUENCE: 21

```
Met Ala Val Glu His Ile Gln Glu Thr Asp Thr Leu Asn Arg Gly Arg
1               5                   10                  15

Ile Lys Ile Asn Glu Ala Ile Asp Leu Ala Asn Asn Ser Ser Thr Lys
            20                  25                  30

Val Asp Gln Phe Glu Ile Asp Leu Ala Gln Gly Ile Gln Asp Ala Lys
                35                  40                  45

Lys Ile Ala Thr Asp Ala Gly Ser Glu Ala Lys Ser Ile Ala Glu Thr
    50                  55                  60

Ala Gly Asn Glu Ala Lys Gln Thr Ala Ser Thr Ala Ala Ile Glu Ala
65                  70                  75                  80

Lys Thr Ile Ala Glu Thr Ala Gly Asn Glu Lys Ala Ile Ala Glu
                85                  90                  95

Asn Ala Gly Leu Glu Ala Asn Lys Lys Ala Asp Gln Ala Ile Ala Asp
                100                 105                 110

Ser Lys Thr Ala Val Asp Asn Ser Asn Gln Ala Ile Gly Arg Ala Asn
            115                 120                 125

Gln Asn Lys Gln Glu Phe Asp Ala Leu Arg Asn Asp Phe Asp Asp Leu
        130                 135                 140

Val Ala Glu Ser Gly Asp Ser Asn Pro Glu Ile Val Gln Ala Arg Thr
145                 150                 155                 160

Asp Thr Gln Gly Val Lys Gln Ser Thr Leu Gln Asn Arg Leu Ile Ala
                165                 170                 175

Asp Phe Ser Thr Arg Leu Thr Asn Ala Asp Ala Ile Gln Leu Phe Ser
                180                 185                 190

Gly Pro Val Asn Val Pro Lys Met Met Asp Leu Ala Gly Lys Val Ala
            195                 200                 205

Gly Asn Ile Glu Ala Asn Pro His Ser Val Tyr Thr Asp Tyr Thr Ala
        210                 215                 220

Thr Ser Leu Lys Thr Pro Ser Ala Ser Trp Ala Glu Ile Thr Gln Glu
225                 230                 235                 240

Asn Tyr Asn Lys Leu Val Gly Arg Asp Asp Gln Gly Val Ser Val Gly
                245                 250                 255

Ser Ser Gln Gly Ser Val Ile Pro Gln Gln Leu Ser Lys Phe Asp Thr
                260                 265                 270

Val Lys Ala Ile Glu Gln Leu Ala Pro Arg Ile Phe Glu Gly Met Ser
            275                 280                 285

Val Ser Glu Lys Val Lys Tyr Ile Lys Asp Asn Phe Ile Ser Phe Ser
        290                 295                 300

Ile Thr Thr Arg Ala Lys Ala Ser Ser Pro Asn Asn Lys Asn Ile Lys
305                 310                 315                 320
```

```
Ile Gly Phe Phe Val Glu Ser Ala Asp Ser Tyr Thr Lys Ile Gln
                325                 330                 335

Gly Asp Ala Thr Asp Phe Thr Asp Phe Thr Thr Glu Ile Asn Asp Asn
            340                 345                 350

Asn Phe Ile Asp Ser Asn Gly Phe Ile His Val Leu Ser Tyr Ala Asp
        355                 360                 365

Ser Ser Asn Gly Val Thr Ala Ser Asn Ile Asn Thr Asp Tyr Ile Gly
    370                 375                 380

Val Gln Leu Met Val Ser Leu Asn Pro Leu Thr Val Leu Asn Lys Ser
385                 390                 395                 400

Gly Phe Ala Asn Glu Asp Asp Leu Ala Leu Lys Val Asp Lys Thr Glu
                405                 410                 415

Phe Gln Lys His Leu Asp Asp Glu Glu Asn Pro His Ser Val Thr Ala
            420                 425                 430

Asn Gln Val Gly Ala Tyr Ser Arg Glu Glu Ser Ser Glu Lys Phe Ala
        435                 440                 445

Glu Lys Thr Glu Leu Thr Lys Glu Lys Val Gly Leu Gly Leu Val Asp
    450                 455                 460

Asn Tyr Glu Thr Ala Ser Gln Asn Asp Ala Glu Glu Gly Gln Val Ser
465                 470                 475                 480

Asn Lys Phe Met Thr Pro Gln Arg Thr Ser Gln Thr Ile Thr Lys Arg
                485                 490                 495

Ile Ala Thr Asp Glu Glu Ala Ile Ile Gly Thr Asn Ile Asn Lys Leu
            500                 505                 510

Ile Thr Pro Lys Val Leu Glu Thr Tyr Gln Asp Arg Thr Lys Val
        515                 520                 525

Ala Val Ala Asn Tyr Gly Thr Gln Asp Val Thr Leu Thr Ala Lys Asp
    530                 535                 540

Lys Leu Thr Glu Ala Ser Trp Arg Tyr Arg Arg Ile Gly Asn Ile Ile
545                 550                 555                 560

Glu Phe Tyr Gly Arg Phe Asn Phe Lys Ala Ala Thr Asp Ile Val Asn
                565                 570                 575

Val Gln Glu Leu Pro Val Gly Phe Arg Leu Ser Ser Asp Phe Asp Asp
            580                 585                 590

Thr Ser Trp Asn Val Pro Leu Asn Ile Gln Lys Ala Ala Asn Pro Thr
        595                 600                 605

Ala Tyr Val Ala Gly Ala Phe Val Glu Arg Gln Gly Thr Asn Leu Leu
    610                 615                 620

Arg Ile Gly Ser Asn Ser Thr Gly Asn His Tyr Val Ser Gly Arg Trp
625                 630                 635                 640

Tyr Thr Asp Asp Pro Phe Pro Thr Gly
                645

<210> SEQ ID NO 22
<211> LENGTH: 240
<212> TYPE: PRT
<213> ORGANISM: Enterococcus faecium

<400> SEQUENCE: 22

Met Val Glu Asn Leu Arg Leu Ser Ala His Arg Gly Ala His Thr Val
1               5                   10                  15

Ala Pro Glu Asn Thr Val Glu Ala Tyr Gln Lys Ala Ile Asp Leu Ser
            20                  25                  30

Tyr Arg Ala Ile Glu Leu Asp Pro Arg Ile Ser Ser Ala Gly Glu Ile
```

```
                35                  40                  45
Phe Ile Met His Asp Asp Thr Val Asp Arg Thr Thr Asn Gly Thr Gly
 50                  55                  60

Tyr Ile Ala Asp Met Ser Ser Glu Gln Ile Arg Gln Leu Glu Ile Asp
 65                  70                  75                  80

Ala Ser Asp Tyr Pro Glu Tyr Gln Ser Lys Val Leu Arg Val Pro Thr
                 85                  90                  95

Phe Glu Glu Ser Val Lys Ile Ile Ser Thr Gly Asp Ile Ile Leu Asn
                100                 105                 110

Val Asp Gly Ser Lys Val Asp Trp Ser Asn Ala Ile Phe Ala Lys Lys
            115                 120                 125

Ala Val Asp Ile Leu Lys Lys Tyr Gly Val Tyr Lys Lys Ser Phe Phe
            130                 135                 140

Val Ile Ser Asp Val Asn Gln Arg Ile Lys Phe Asn Glu Ser Tyr Pro
145                 150                 155                 160

Asp Ala Thr Leu Ser Trp Leu Leu Thr Asp Glu Asn Leu Ile Asp Ser
                165                 170                 175

Ala Ile Ser Glu Ala Lys Lys Tyr Gln Arg Ala Leu Leu Ser Ile Pro
            180                 185                 190

Leu Glu Leu Ala Thr Glu Val Val Phe Glu Lys Leu Arg Asn Thr Asn
            195                 200                 205

Ile Tyr Tyr Gln Ile Tyr Asn Val Asn Arg Ile Ile Asp Leu Lys Tyr
        210                 215                 220

Leu Thr Ser Lys Lys Val Arg Met Val Glu Thr Asp Thr Leu Leu Pro
225                 230                 235                 240

<210> SEQ ID NO 23
<211> LENGTH: 269
<212> TYPE: PRT
<213> ORGANISM: Enterococcus faecium

<400> SEQUENCE: 23

Val Lys Lys Ile Leu Gly Thr Leu Ile Ala Phe Ser Phe Val Leu Thr
  1               5                  10                  15

Gly Cys Val Ser Ala Ser Asn Asn Leu Leu Ser His Lys Glu Thr Tyr
                 20                  25                  30

Leu Val Ala His Arg Gly Ala His Ile Val Ala Pro Glu Asn Thr Val
             35                  40                  45

Glu Ala Met Arg Glu Ala Lys Leu Leu Gly Tyr Asn Ala Val Glu Val
 50                  55                  60

Asp Val Arg Thr Ser Lys Asp Gly Val Asn Phe Leu Met His Asp Asp
 65                  70                  75                  80

Thr Leu Asp Arg Thr Thr Asn Gly Glu Gly Gln Pro Glu Arg Leu Thr
                 85                  90                  95

Ile Lys Gln Leu Lys Glu Leu Ser Val Asp Thr Ser Asn Tyr Pro Lys
                100                 105                 110

Tyr Lys Asp Lys Lys Val Asn Ile Pro Thr Phe Asp Glu Ala Ile Lys
            115                 120                 125

Glu Ile Ser Lys Asp Lys Leu Ile Val Asn Val Asp Gly Ser Lys Gly
            130                 135                 140

Glu Trp Asp Asn Asn Asp Phe Val Asn Ser Ile Val Ser Thr Leu Lys
145                 150                 155                 160

Lys Tyr Asn Val Tyr Asp Arg Ser Phe Phe Val Leu Thr Asn Lys Glu
                165                 170                 175
```

-continued

Ile Arg Asp Asn Val Val Lys Ser His Pro Asp Cys Thr Val Ser Trp
            180                 185                 190

Leu Tyr Asp Ser Lys Asn Ser Ile Asp Glu Ile Gln Gln Val Lys
        195                 200                 205

Gln Tyr Asn Lys Ala Leu Leu Ser Val Ser Asn Thr Leu Ala Thr Asp
    210                 215                 220

Gln Leu Ile Glu Lys Leu Asn Lys Ser Gly Ile Met Tyr Gln Ile Tyr
225                 230                 235                 240

Gly Val Asn Asp Ile Gln Arg Phe Lys Lys Leu Lys Ser Leu Asp Val
                245                 250                 255

Pro Ile Val Glu Thr Asp Thr Ile Asn Pro Asn Glu Ile
            260                 265

<210> SEQ ID NO 24
<211> LENGTH: 689
<212> TYPE: PRT
<213> ORGANISM: Artificial Sequence
<220> FEATURE:
<223> OTHER INFORMATION: Synthetic sequence

<400> SEQUENCE: 24

Met Leu Met Ala Leu Asp Leu Lys Arg Thr Tyr Thr Ala Ile Leu Asp
1               5                   10                  15

Asn Ala Tyr Gln Val Ser Tyr Glu Lys Ile Glu Asn Lys Ile Gly Ser
            20                  25                  30

Leu Asp Phe Thr Met Pro Leu Asp Asp Pro Lys Asn Glu Phe Ile Ala
        35                  40                  45

Glu Met Gln Trp Val Glu Leu Thr Asp Asn Glu Asn Glu Tyr Ile Gly
    50                  55                  60

Leu Tyr Arg Val Met Pro Thr Thr Ile Lys Lys Asp Ala Asn Asn Asn
65                  70                  75                  80

Gln Ile His Tyr Ser Ala Thr Glu Ala Leu Cys Thr Leu Gly Asp Thr
                85                  90                  95

Val Leu Phe Gly Cys His Glu Ile Lys Asn Lys Thr Thr Lys Glu Ala
            100                 105                 110

Ile Gln Phe Leu Leu Asn Lys Gln Lys Thr Lys His Trp Val Leu Lys
        115                 120                 125

Lys Cys Asp Phe Ser Arg Lys Leu Thr Tyr Lys Trp Glu Asn Glu Asn
130                 135                 140

Gly Leu Val Glu Pro Leu Phe Ser Ile Pro Ala Asp Phe Glu Glu Glu
145                 150                 155                 160

Tyr Leu Trp Gln Trp Asn Thr Glu Val Tyr Pro Phe Glu Leu Ser Leu
                165                 170                 175

Val Lys Pro Pro Thr Glu Pro Val Ala Arg Ile Gln Glu Gly Tyr Asn
            180                 185                 190

Met Gln Gly Phe Glu Ile Glu Arg Asn Pro Lys Met Leu Ile Asn Arg
        195                 200                 205

Ile Tyr Pro Leu Gly Ser Gly Glu Gly Val Asn Lys Val Asn Ile Arg
    210                 215                 220

Ser Val Asn Gln Gly Val Pro Tyr Leu Glu Asn Lys Ala Ala Ile Asp
225                 230                 235                 240

Arg Tyr Gly Leu Leu Glu Ser Ile Trp Val Glu Gln Arg Phe Ser Asp
                245                 250                 255

Pro Lys Ala Leu Lys Glu Asn Ala Leu Arg Met Leu Glu Glu Trp Thr
            260                 265                 270

```
Lys Pro Gln Val Ser Trp Val Val Thr Ala Ala Asp Leu Ile Lys Leu
            275                 280                 285

Thr Asp Gln Pro Leu Ala Ile Asp Arg Leu Arg Leu Gly Thr Val Ile
        290                 295                 300

Met Ile Asn Thr Asn Glu Phe Gly Ser Val Asn Leu Arg Ile Lys Lys
305                 310                 315                 320

Glu Ser Lys Lys Asp Val Phe Gly Ala Pro Gln Asp Ile Gln Leu Glu
                325                 330                 335

Leu Gly Asn Leu Gln Glu Thr Ile His Ser Thr Met Thr Ala Phe Ser
            340                 345                 350

Arg Lys Gln Glu Ile Asn Glu Thr Tyr Ala Gln Gly Ala Thr Thr Leu
        355                 360                 365

Leu Asn Arg Ser Ile Gln Gly Glu Leu Ser Lys Thr Gln Pro Val Glu
    370                 375                 380

Leu Asn Leu Tyr Phe Asp Glu Asp Ile Leu Tyr Ile Asn Thr Ala Glu
385                 390                 395                 400

Leu Thr Phe Lys Thr Lys Arg Tyr Arg Gly Tyr Thr Lys Ala Val Lys
                405                 410                 415

Gly Gly Gly Ala Lys Thr Ile Thr Ser Glu Ala Gly Gly Gln Ser Thr
            420                 425                 430

Gln Thr Ser Ser Ala Gly Gly Ser Arg Gln Thr Ser Ser Ala Gly
        435                 440                 445

Gly Gly Ser Val Gln Ser Thr Thr Ala Gly Gly Gly Val Thr Thr
    450                 455                 460

Ser Gly Ser Gly Gly Ser Tyr Gln Gly Ser Ser Thr Ser Val Gly
465                 470                 475                 480

Gly Gly Ser Thr Gln Thr Ser Ser Ala Asn Gly Thr His Arg His Met
                485                 490                 495

Met Phe Glu Ser Val Asp Ala Ser Gly Pro Ile Gln Thr Thr Arg Tyr
            500                 505                 510

Lys Ala Tyr Gly Ser Ser Leu Met Gln Met Gln Gly Ser Pro Gly Lys
        515                 520                 525

Ile Tyr Thr Ala Glu Ala Ala Asp Asn His Thr His Thr Val Asn Ile
    530                 535                 540

Pro Asn His Ser His Asn Phe Thr Ile Asn Val Pro Ala His Thr His
545                 550                 555                 560

Asn Val Ser Ile Pro Ser His Ala His Ser Val Asn Ile Pro Asn His
                565                 570                 575

Thr His Ser Val Asn Ile Pro Asn His Thr His Thr Val Lys Ile Pro
            580                 585                 590

Ser His Lys His Asn Val Val Leu Pro Glu His Thr His Pro Leu Glu
        595                 600                 605

Trp Gly Ile Phe Gln Ala Ser Asp Ser Pro Ser Ser Val Asp Ile Val
    610                 615                 620

Val Asp Gly Lys Thr Ile Pro His His Glu Thr Ser Gln Asn Arg Leu
625                 630                 635                 640

Asn Leu Val Asp Tyr Leu Lys Lys Thr Ser Ser Gly Gln Ile Gln Arg
                645                 650                 655

Gly Ser His Thr Ile Gln Ile Lys Pro Asn Lys Leu Ala Arg Ile Glu
            660                 665                 670
```

```
Ala Gln Val Thr Cys Arg Val Phe Ile Gln Ser Gln Leu Gly Gly Gln
        675                 680                 685
Phe
```

ENTEROCINS AND METHODS OF USING THE SAME

BACKGROUND OF THE INVENTION

Field of the Invention

This application relates generally to the identification, isolation, modification, and expression, of a cluster of genes sufficient to produce an enterocin, and more specifically, a Phage tail-like bacteriocin (PTLB) that specifically kills *Enterococcus* species; and methods to alter its bactericidal specificity, produce, and use the same.

Background Information

*Enterococcus* is a genus of bacteria that includes more than forty species. *Enterococci* are gram-positive cocci that are facultative anaerobes (i.e., are capable of surviving in the presence or absence of oxygen). The major human pathogen in the genus *Enterococcus* is *Enterococcus faecalis*, although *Enterococcus faecium* has recently become prevalent in nosocomial infections. Other *Enterococci* associated with human infections include, for example, *Enterococcus gallinarum, Enterococcus casseliflavus, Enterococcus avium, Enterococcus cecorum, Enterococcus durans, Enterococcus hirae, Enterococcus malodoratus, Enterococcus mundtii, Enterococcus pseudoavium* and *Enterococcus raffinosus*.

Although *Enterococci* are generally not as virulent as many other gram-positive cocci, and often arise in debilitated or immunocompromised individuals, their increasing resistance to antimicrobial agents has led to their proliferation as opportunistic pathogens, particularly in patients receiving broad-spectrum antibiotics. For instance, Vancomycin-Resistant *Enterococci* (VRE) have acquired resistance to most commonly-used antibiotics in addition to vancomycin, and therefore, can be challenging to treat; even though VRE may show sensitivity to a few antibiotics, this sensitivity often reflects the infrequent use of these latter antibiotics in the clinical setting, due to their toxicity or side-effects. This makes their use as a last line of defense problematic. Additionally, *Enterococci* have recently been implicated in a wide range of disorders related to their presence as components of the gut microbiota.

Aside from low molecular weight antibiotic compounds, it is known that some bacteria produce high molecular weight protein structures, termed phage tail-like bacteriocins (PTLBs), that function to kill competing bacterial strains or species. See, e.g., Scholl D. ("Phage tail-like bacteriocins," *Annu. Rev. Virology*, 2017, 29: 453-467). There are two major types of PTLBs: R-type and F-type: R-type PTLBs have a contractile mechanism of action, and are evolutionarily related to the tail structures of Myoviridae bacteriophages ("phages"); in contrast, F-type PTLBs are non-contractile, and are related to the tail structures of Siphoviridae phages. Both R-type- and F-type PTLBs kill bacterial cells by first binding to specific targets ("receptors") on the bacterial cell surface via Receptor Binding Proteins (RBPs); and then the bound bacteriocins create a channel in the cell envelope that results in death of the targeted bacterium. These nano-scale structures can be adapted as antimicrobial agents to, for example, treat disease in humans and animals; decontaminate food products and surfaces; and manipulate the composition of a microbiome.

Most PTLBs have a very limited binding and killing spectrum, typically killing specific strains within the same species that produce them; although narrow spectrum, or targeted, antimicrobials have advantages over broad-spectrum antibiotics, the bactericidal spectra of PTLBs are often too narrow for practical use. Hence, to transform PTLBs into more practical antimicrobials, it is desirable to expand their binding/killing spectra such that they may cover all, or nearly all, the members of an entire species, rather than only selected strains of the species.

Although PTLBs are found in various different bacteria, no PTLBs have previously been reported to be produced by, or have activity against, *Enterococci*. *Enterococci* are, however, known to harbor prophages. One recent study sought to characterize all of the prophages detectable within *Enterococcus faecalis*. See, e.g., Matos et al. ("*Enterococcus faecalis* prophage dynamics and contributions to pathogenic traits," *PLOS Genet.*, 2013, 9(6): e1003539), but did not report finding any PTLBs.

SUMMARY OF THE INVENTION

In one aspect of the present disclosure, the present inventors discovered that a locus (pp2) in *E. faecalis* previously identified as a prophage, see Matos et al. ("*Enterococcus faecalis* prophage dynamics and contributions to pathogenic traits," *PLOS Genet.*, 2013, 9(6): e1003539), actually encoded a PTLB. To elucidate this, the present inventors cloned the entire gene cluster of pp2 into *Bacillus subtilis*, and expressed the genes under the control of an inducible promoter. After analysis of the complex structure of the resulting product by electron microscopy, the present inventors identified that the product exhibited the morphological features of an F-type PTLB, including the absence of a head-like structure required of a phage.

In addition, the identified, cloned, expressed and purified structure displayed antimicrobial activity against many different strains of *Enterococci*. Hence, the present inventors discovered that this genetic locus encoded a PTLB, or an "enterocin," and not a phage as had previously been reported. The present inventors have thus described, for the first time, a PTLB for the *Enterococcus* genus.

Non-limiting embodiments of the present disclosure include as follows:

(1) An isolated nucleic acid molecule encoding an enterocin, wherein the nucleic acid molecule comprises a first polynucleotide sequence that encodes the structural proteins of a functional enterocin except the corresponding natural receptor binding protein (RBP) and the corresponding natural adaptor protein containing the Base Plate Attachment Region (BPAR); wherein the structural proteins encoded by the first polynucleotide sequence are at least 80% identical to SEQ ID NOs: 4-14; wherein the nucleic acid molecule further comprises a heterologous second polynucleotide sequence encoding a heterologous RBP; and wherein the enterocin has bactericidal specificity against at least one strain of an *Enterococcus* species, or other genus of bacteria as determined by the heterologous RBP, and the specificity is different from that determined by the natural RBP of the natural enterocin.

(2) The nucleic acid molecule of (1), wherein said nucleic acid molecule further comprises a third polynucleotide sequence encoding a heterologous adaptor protein, wherein said heterologous adaptor protein links said heterologous RBP to the structural proteins encoded by said first polynucleotide sequence; and wherein said heterologous adaptor protein comprises a BPAR native to the structural proteins encoded by the first polynucleotide sequence.
(3) The nucleic acid molecule of (2), wherein the BPAR is located at or towards the N-terminus of said heterologous adaptor protein.
(4) The nucleic acid molecule of (2), wherein the heterologous adaptor protein includes an amino acid sequence at least 80% identical to residues 1-369 of SEQ ID NO: 15.
(5) The nucleic acid molecule of (2), wherein the encoded heterologous adaptor protein further comprises at least a part of an adaptor protein of a prophage or prophage remnant from the genome of a gram positive bacterium; or comprises at least a part of an adaptor protein of a bacteriophage that infects a gram positive bacterium.
(6) The nucleic acid molecule of (5), wherein said part of an adaptor protein of a prophage or prophage remnant from the genome of a gram positive bacterium, or said part of an adaptor protein of a bacteriophage that infects a gram positive bacterium, is located at or towards the C-terminus of said heterologous adaptor protein.
(7) A vector comprising the nucleic acid molecule of any one of (1) to (6), wherein the nucleic acid molecule is operably linked to a small molecule-induced promoter.
(8) The vector of (7), wherein the promoter is placed at 11, 14, 17, 20, or 23 nucleotides upstream of the portion of the nucleic acid encoding a polypeptide at least 80% identical to SEQ ID NO: 4.
(9) An isolated nucleic acid molecule encoding an enterocin, wherein the nucleic acid molecule comprises a first polynucleotide sequence that encodes polypeptides at least 80% identical to SEQ ID NOs: 4-16, operably linked to a heterologous promoter inducible by a small molecule; wherein the encoded enterocin has bactericidal activity against at least one strain of an *Enterococcus* species; and wherein the first polynucleotide sequence is operably linked to the heterologous promoter.
(10) The nucleic acid molecule of (9), wherein the promoter is placed at 11, 14, 17, 20, or 23 nucleotides upstream of the portion of the nucleic acid encoding a polypeptide at least 80% identical to SEQ ID NO: 4.
(11) An enterocin producer cell comprising a first foreign polynucleotide sequence that encodes structural polypeptides at least 80% identical to SEQ ID NOs: 4-14, and further comprising a second foreign polynucleotide sequence encoding a heterologous RBP; wherein the bactericidal specificity of the enterocin is determined by the heterologous RBP; and wherein the first and second foreign polynucleotide sequences are located in the same nucleic acid molecule or are located in separate nucleic acid molecules.
(12) A producer cell of (11), wherein the first and second foreign polynucleotide sequences are in separate nucleic acid molecules.
(13) The producer cell of (11), wherein said producer cell further comprises a third foreign polynucleotide sequence encoding a heterologous adaptor protein, wherein in said enterocin, said heterologous adaptor protein links said heterologous RBP to the structural proteins encoded by said first polynucleotide sequence, and wherein said heterologous adaptor protein comprises a BPAR native to the structural proteins encoded by the first polynucleotide sequence.
(14) The producer cell of (13), wherein the BPAR is located at or towards the N-terminus of said heterologous adaptor protein.
(15) The producer cell of (13), wherein the heterologous adaptor protein includes an amino acid sequence at least 80% identical to residues 1-369 of SEQ ID NO: 15.
(16) The producer cell of (13), wherein the encoded heterologous adaptor protein further comprises at least a part of an adaptor protein of a prophage or prophage remnant from the genome of a gram positive bacterium; or comprises at least a part of an adaptor protein of a bacteriophage that infects a gram positive bacterium.
(17) The producer cell of (16), wherein said part of an adaptor protein of a prophage or prophage remnant from the genome of a gram positive bacterium, or said part of an adaptor protein of a bacteriophage that infects a gram positive bacterium, is located at or towards the C-terminus of said heterologous adaptor protein.
(18) An enterocin encoded by the nucleic acid molecule of any one of (1)-(6), (9) or (10).
(19) A method of killing an *Enterococcus* species in vivo, comprising contacting the *Enterococcus* with an effective amount of the enterocin of (18), whereby the enterocin binds and kills the *Enterococcus*.
(20) The method of (19), wherein the contacting is to an *Enterococcus* on a surface contaminated with *Enterococcus*.
(21) The nucleic acid molecule of (4), wherein the adaptor protein comprises amino acids identical to those at positions 364 and 365 of SEQ ID NO: 15.
(22) The enterocin of (18), or the producer cell of (11), for use in a method of treating an *Enterococcus* infection in an animal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A depicts an electron micrograph of purified enterocin particles produced in *B. subtilis*. FIG. 2B depicts the results of a quantitative survival assay showing bactericidal activity against a susceptible *Enterococcus* isolate.

FIG. 3. Bactericidal activity of recombinant enterocins on a panel of *E. faecium* and *E. faecalis*. The + and − signs signify semi-quantitative levels of killing of the indicated target species, or lack of killing, respectively.

FIG. 5 depicts a comparison between wild-type enterocin and a non-natural bacteriocin (Av-ENcun41) of the present disclosure. A fusion was made between the N-terminus of a portion of the enterocin BPAR and a C-terminal portion of the cun41 BPAR (speckled appearance). The C-terminal end of the cun41 BPAR interacts with the N-terminal end of the cun41 RBP. Also included in the Av-ENcun construct are two downstream genes that were important for RBP function.

DETAILED DESCRIPTION OF THE INVENTION

Figure 1:
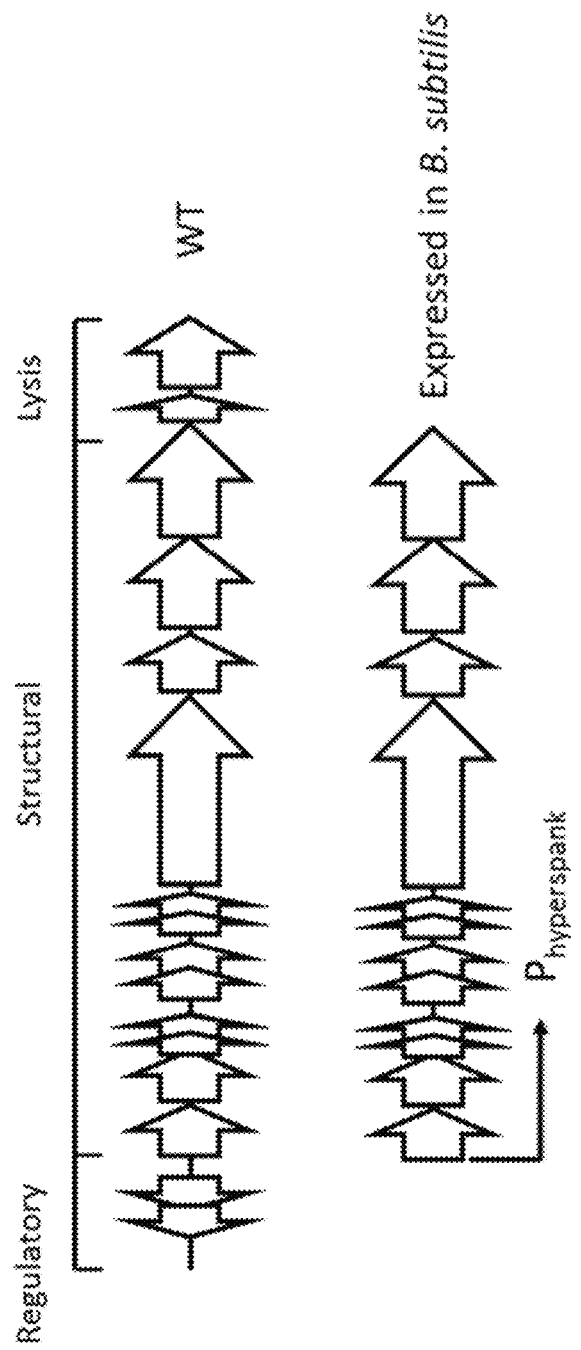
FIG. 1. Structure of the S32 enterocin genetic locus cloned and expressed in *B. subtilis*. The holin and lysin (lysis genes) were deleted to prevent unwanted lysing of the producer cells upon induction. The natural regulatory genes were replaced with the $P_{hyperspank}$ promoter, which was inducible with IPTG.

The present invention is based on the identification, cloning, and expression of a genetic locus within an *Enterococcus* genome that encodes a Phage tail-like bacteriocin (PTLB), termed an enterocin. Also provided are modified or non-natural enterocins, such as those that have been engineered to have altered bactericidal specificity. Further, provided herein are nucleic acid molecules encoding natural or non-natural enterocins, integration vector constructs containing such nucleic acids operably linked to a heterologous promoter, producer cells that do not naturally produce enterocins but containing such nucleic acid molecules or vectors, the encoded enterocins, and methods of making and using such enterocins.

As used interchangeably herein, the terms "Phage tail-like bacteriocin" (PTLB) and high molecular weight (HMW) bacteriocin may include, F-type bacteriocins (FTBs) and R-type bacteriocins (RTBs). For example, an enterocin is a PTLB.

The term "enterocin" refers to a PTLB isolated from, or derived from, an *Enterococcus* species. Enterocins disclosed herein are complex molecules comprising multiple protein, or polypeptide, subunits and distantly resemble the tail structures of bacteriophages. In naturally occurring enterocins, the subunit structures are encoded by a genetic locus present within the bacterial genome such as that of *E. faecium*, or *E. faecalis*. Enterocins may be natural or non-natural.

The present disclosure further relates to the identification, cloning, and expression of a genetic locus within an *Enterococcus* genome that, as a cluster of genes, encodes a Phage tail-like bacteriocin (PTLB), hereby termed an enterocin. The present disclosure also relates to modified enterocins. Enterocins contain a receptor binding protein (RBP) that directs the binding of the enterocin to the bacterium that it kills.

In one aspect, the present disclosure provides an isolated nucleic acid molecule(s) encoding a non-natural enterocin, wherein the nucleic acid molecule(s) contains a first polynucleotide sequence that encodes an enterocin structural scaffold; a second polynucleotide sequence encoding a heterologous RBP; and a third polynucleotide sequence encoding an RBP adaptor protein. The first, second and third polynucleotide sequences may be present in the same, or in different, nucleic acid molecules. The enterocin has bactericidal specificity as determined by the heterologous RBP.

In some embodiments, the scaffold contains all structural proteins of a functional enterocin except an RBP and an RBP adaptor protein. In certain embodiments, the open-reading frames encoding the proteins constituting the structural scaffold need not be located on the same nucleic acid molecule, but preferably, are encoded by a single polynucleotide sequence. In some embodiments, the enterocin scaffold encoded by the first polynucleotide sequence comprises polypeptides at least 80%, 85%, 86%, 87%, 88%, 89%, 90%, 91%, 92%, 93%, 94%, 95%, 96%, 97%, 98%, or at least 99% identical, to SEQ ID NOs: 4-14. In some embodiments, any one or more of the polypeptides in the structural scaffold may have at least 85%, 86%, 87%, 88%, 89%, 90%, 91%, 92%, 93%, 94%, 95%, 96%, 97%, 98%, or at least 99% identity, to the corresponding polypeptide(s) in the enterocin structural scaffold encoded by the open reading frames (ORFs) corresponding to genes 1278-1289 of *E. faecalis* isolate S32. In some embodiments, the scaffold includes the proteins encoded by the ORFs corresponding to genes 1278-1289 of *E. faecalis* isolate S32.

The RBP adaptor protein acts as an adaptor between the enterocin structural scaffold, particularly the enterocin baseplate, and an RBP (such as, for example, a heterologous RBP). The RBP adaptor protein may comprise, or consist of, for example, two domains: an N-terminal Base Plate Attachment Region (BPAR) as a first domain; and a C-terminal region that interacts with the RBP as a second domain. An example of a natural adaptor protein is SEQ ID NO: 15. In some embodiments, the adaptor protein includes at least a BPAR-containing region, or part thereof, of SEQ ID NO: 15.

In some embodiments of the present disclosure, the RBP adaptor protein is a non-natural fusion protein comprising an N-terminal portion of an RBP adaptor protein native to the enterocin scaffold but fused to the C-terminal portion of an RBP adaptor protein from a different PTLB, such as a different enterocin; or from a phage, or prophage, for example. Such a non-natural adaptor protein can therefore be used to link an enterocin scaffold to a heterologous RBP.

In some embodiments, the BPAR in the adaptor protein is native to the structural scaffold. In other embodiments, the BPAR is highly homologous to the BPAR native to the structural scaffold. In particular embodiments, the BPAR is at least 80% identical to the BPAR native to the structural scaffold. In other embodiments, the BPAR is at least 85%, 86%, 87%, 88%, 89%, 90%, 91%, 92%, 93%, 94%, 95%, 96%, 97%, 98%, or at least 99% identical, to the BPAR native to the structural scaffold.

In particular embodiments, the adaptor protein contains, at or towards the N-terminus, the first 100, 150, 200, 225, 250, 275, 300, 325, 350, 375, 400, 425, 450, 475, or 500 residues of an adaptor protein native to an enterocin (including, but not limited to, SEQ ID NO: 15), counting from the N-terminus. In some embodiments, the adaptor protein contains the first 360, 361, 362, 363, 364, 365, 366, 367, 368 or 369 residues of SEQ ID NO: 15, counting from the N-terminus. In other embodiments, the adaptor protein contains, at or towards the N-terminus, a sequence that is at least 80%, 85%, 86%, 87%, 88%, 89%, 90%, 91%, 92%, 93%, 94%, 95%, 96%, 97%, 98%, or at least 99% identical, to the first 100, 150, 200, 225, 250, 275, 300, 325, 350, 375, 400, 425, 450, 475, or 500 residues of SEQ ID NO: 15, counting from the N-terminus. In some embodiments, the adaptor protein contains, at or towards the N-terminus, a sequence that is at least 80%, 85%, 86%, 87%, 88%, 89%, 90%, 91%, 92%, 93%, 94%, 95%, 96%, 97%, 98%, or at least 99% identical, to the first 360, 361, 362, 363, 364, 365, 366, 367, 368 or 369 residues of SEQ ID NO: 15, counting from the N-terminus.

In another aspect, there are provided producer cell integration vectors containing the disclosed nucleic acid molecule(s) encoding an enterocin, wherein the nucleic acid molecule is operably linked to a heterologous inducible promoter. In certain embodiments, the producer cell is *B. subtilis*. *B. subtilis* does not naturally produce an enterocin.

In still another aspect, the present disclosure provides a nucleic acid molecule(s) encoding all or part of an enterocin, wherein the nucleic acid molecule(s) comprises a polynucleotide sequence that encodes polypeptides at least 80%, 85%, 86%, 87%, 88%, 89%, 90%, 91%, 92%, 93%, 94%, 95%, 96%, 97%, 98%, or at least 99% identical, to SEQ ID NOs: 4-14, operably linked to a heterologous promoter.

In some embodiments, the promoter is placed at approximately 11, 14, 17, 20, or 23 nucleotides upstream of the portion of the polynucleotide sequence encoding a polypeptide at least 80%, 85%, 86%, 87%, 88%, 89%, 90%, 91%, 92%, 93%, 94%, 95%, 96%, 97%, 98%, or at least 99% identical, to SEQ ID NO: 4. In other embodiments, the promoter is placed at approximately 11, 14, 17, 20, or 23 nucleotides upstream of the portion of a polynucleotide sequence encoding SEQ ID NO: 4.

In a further aspect, there are provided enterocin producer cells containing the disclosed nucleic acid molecule(s) encoding an enterocin.

In some embodiments, the enterocin producer cell contains a first foreign polynucleotide sequence encoding polypeptides at least 80%, 85%, 86%, 87%, 88%, 89%, 90%, 91%, 92%, 93%, 94%, 95%, 96%, 97%, 98%, or at least 99% identical, to SEQ ID NOs: 4-14. The enterocin producer cell may also contain a second foreign polynucleotide sequence encoding an RBP. The enterocin producer cell may also contain a third foreign polynucleotide sequence encoding an RBP adaptor protein, which acts as an adaptor between the enterocin scaffold and the RBP, such as a heterologous RBP. An example of a natural adaptor protein is SEQ ID NO: 15. The producer cell thus produces an enterocin having bactericidal specificity as determined by the RBP. Any or all of the first, second and third polynucleotide sequences may be present on the same, or different, nucleic acid molecule(s).

In some embodiments, the RBP adaptor protein encoded by the producer cell is a non-natural fusion protein, comprising an N-terminal portion of an RBP adaptor protein native to the enterocin scaffold fused to the C-terminal portion of an RBP adaptor protein from a different PTLB, such as a different enterocin; or from a phage, or prophage, for example.

In yet another aspect, there are provided methods of producing an enterocin, by exposing an enterocin producer cell containing one or more nucleic acid molecules encoding an enterocin, wherein the nucleic acid molecule is operably linked to a heterologous inducible promoter, to an inducing agent in a concentration effective to induce expression of the enterocin via the inducible promoter, thereby producing the enterocin.

In some embodiments, the nucleic acid molecule(s) encoding an enterocin is integrated within the genome of the producer cell, in order to generate a stable enterocin producer cell.

In another aspect, there are provided methods of killing *Entercocci*, comprising contacting an *Enterococcus* species or strain with an effective amount of an enterocin of the present disclosure, whereby the enterocin binds and kills the *Enterococcus* species or strain. In some embodiments, the contacting is with a surface contaminated with *Enterococci*. In one example, the contacting is at 2-10° C.

In yet another aspect, there are provided methods of treating an *Enterococcus* infection, or colonization, in an animal, comprising administering to an animal in need thereof a therapeutically-effective amount of an enterocin of the present disclosure; or an enterocin producer cell of the present disclosure, in an amount sufficient to produce a bactericidal amount of the enterocin, thereby treating the *Enterococcus* infection or colonization.

"Natural enterocins" as used herein refer to those enterocins that exist in nature, and include native particles obtained from *Enterococcus*, as well as particles obtained through expression of a natural enterocin gene cluster in an enterocin producer cell that does not in nature produce an enterocin.

"Non-natural enterocins" as used herein refer to those enterocins that do not exist in nature. In some embodiments, the non-natural enterocin contains a heterologous RBP. A "heterologous RBP" may be a native RBP obtained from a different source than was the structural scaffold to which it is attached; or a heterologous RBP may be a modified RBP that was a natural RBP prior to being intentionally modified or mutated to change its physical and/or biological properties. In some embodiments, a modified RBP is one that contains an amino acid sequence that is different (e.g., engineered to differ) from a native or natural RBP and confers to the resulting non-natural enterocin different receptor binding properties. For instance, a modified RBP may have a sequence that is at least 85%, 86%, 87%, 88%, 89%, 90%, 91%, 92%, 93%, 94%, 95%, 96%, 97%, 98%, or even 99% identical to a native or natural RBP.

As used herein, the terms "nucleic acid sequence," "nucleotide sequence," and "oligonucleotide" are interchangeable and refer to a polymeric form of nucleotides. As used herein, the term "polynucleotide" refers to a polymeric form of nucleotides that has one 5' end and one 3' end and can comprise one or more nucleic acid sequences. The nucleotides may be deoxyribonucleotides (DNA), ribonucleotides (RNA), analogs thereof, or combinations thereof, and may be of any length. Polynucleotides may perform any function and may have various secondary and tertiary structures. The terms encompass known analogs of natural nucleotides and nucleotides that are modified in the base, sugar, and/or phosphate moieties. Analogs of a particular nucleotide have the same base-pairing specificity (e.g., an analog of A base pairs with T). A polynucleotide may comprise one or more modified nucleotides. Examples of modified nucleotides include fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. The terms also encompass nucleic acids comprising modified backbone residues or linkages, that are synthetic, naturally occurring, and/or non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (LNA™) (Exiqon, Woburn, MA) nucleosides, glycol nucleic acid, bridged nucleic acids, and morpholino structures.

Polynucleotide sequences are displayed herein in the conventional 5' to 3' orientation unless otherwise indicated.

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., BLAST, CS-BLAST, FASTA, HMMER, L-ALIGN, and the like) available through the worldwide web at sites including, but not limited to, GENBANK (www.ncbi.nlm.nih.gov/genbank/) and EMBL-EBI (www.ebi.ac.uk.). Sequence identity between two polynucleotides or two polypeptide sequences is generally calculated using the standard default parameters of the various methods or computer programs. A high degree of sequence identity between two polynucleotides or two polypeptides is typically between about 90% identity and 100% identity over the length of the reference polypeptide, for example, about 90% identity or higher, preferably about 95% identity or higher, more preferably about 98% identity or higher. A moderate degree of sequence identity between two polynucleotides or two polypeptides is typically between about 80% identity to about 85% identity, for example, about 80% identity or higher, preferably about 85% identity over the length of the reference polypeptide. A low degree of sequence identity between two polynucleotides or two polypeptides is typically between about 50% identity and 75% identity, for example, about 50% identity, preferably about 60% identity, more preferably about 75% identity over the length of the reference polypeptide.

As used herein, "hybridization," "hybridize," or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5° C. to 10° C. below Tm; moderate stringency, approximately 0.16M to approximately 0.33M salt, hybridization temperature 20° ° C. to 29° C. below Tm; and low stringency, approximately 0.33M to approximately 0.82M salt, hybridization temperature 40° C. to 48° C. below Tm. Tm of duplex nucleic acid sequences is calculated by standard methods well-known in the art (see, e.g., Maniatis, T., et al., Molecular Cloning: A Laboratory Manual, Cold Spring Harbor Laboratory Press: New York (1982); Casey, J., et al., Nucleic Acids Research 4:1539-1552 (1977); Bodkin, D. K., et al., Journal of Virological Methods 10(1):45-52 (1985); Wallace, R. B., et al., Nucleic Acids Research 9(4):879-894 (1981)). Algorithm prediction tools to estimate Tm are also widely available. High stringency conditions for hybridization typically refer to conditions under which a polynucleotide complementary to a target sequence predominantly hybridizes with the target sequence, and substantially does not hybridize to non-target sequences. Typically, hybridization conditions are of moderate stringency, preferably high stringency.

As used herein, "complementarity" refers to the ability of a nucleic acid sequence to form hydrogen bonds with another nucleic acid sequence (e.g., through canonical Watson-Crick base pairing). A percent complementarity indicates the percentage of residues in a nucleic acid sequence that can form hydrogen bonds with a second nucleic acid sequence. If two nucleic acid sequences have 100% complementarity, the two sequences are perfectly complementary, i.e., all of the contiguous residues of a first polynucleotide hydrogen bond with the same number of contiguous residues in a second polynucleotide.

As used herein, "binding" refers to a non-covalent interaction between macromolecules (e.g., between a protein and a polynucleotide, between a polynucleotide and a polynucleotide, or between a protein and a protein, and the like). Such non-covalent interaction is also referred to as "associating" or "interacting" (e.g., if a first macromolecule interacts with a second macromolecule, the first macromolecule binds to second macromolecule in a non-covalent manner). Binding interactions can be characterized by a dissociation constant (Kd). "Binding affinity" refers to the strength of the binding interaction. An increased binding affinity is correlated with a lower Kd.

As used herein, the term "operably linked" refers to polynucleotide sequences or amino acid sequences placed into a functional relationship with one another. For example, regulatory sequences (e.g., a promoter or enhancer) are "operably linked" to a polynucleotide encoding a gene product if the regulatory sequences regulate or contribute to the modulation of the transcription of the polynucleotide. Operably linked regulatory elements are typically contiguous with the coding sequence. However, enhancers can function if separated from a promoter by up to several kilobases or more. Accordingly, some regulatory elements may be operably linked to a polynucleotide sequence but not contiguous with the polynucleotide sequence. Similarly, translational regulatory elements contribute to the modulation of protein expression from a polynucleotide.

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene products." Expression may include splicing the mRNA in a eukaryotic cell, if the polynucleotide is derived from genomic DNA.

A "coding sequence," or a sequence that "encodes" a selected polypeptide, is a nucleic acid molecule that is transcribed (in the case of DNA) and translated (in the case of mRNA) into a polypeptide in vitro or in vivo when placed under the control of appropriate regulatory sequences. The boundaries of the coding sequence are determined by a start codon at the 5' terminus and a translation stop codon at the 3' terminus. A transcription termination sequence may be located 3' to the coding sequence.

"Vector" and "plasmid" as used herein refer to a polynucleotide vehicle to introduce genetic material into a cell. Vectors can be linear or circular. Vectors can contain a replication sequence capable of effecting replication of the vector in a suitable host cell (e.g., an origin of replication). Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art. The four major types of vectors are plasmids, viral vectors, cosmids, and artificial chromosomes. Typically, vectors comprise an origin of replication, a multicloning site, and/or a selectable marker. An expression vector typically comprises an expression cassette. By "recombinant virus" is meant a virus that has been genetically altered, e.g., by the addition or insertion of a heterologous nucleic acid construct into a viral genome or portion thereof.

As used herein, "expression cassette" refers to a polynucleotide construct generated using recombinant methods or by synthetic means and comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in a vector to form an expression vector.

The terms "polypeptide", "peptide", and "protein" are typically used interchangeably herein to refer to a polymer of amino acid residues. Amino acids may be referred to herein by either their commonly known three letter symbols or by the one-letter symbols recommended by the IUPAC-IUB Biochemical Nomenclature Commission. A polypeptide may be of any length. It may be branched or linear, it may be interrupted by non-amino acids, and it may comprise modified amino acids. The terms also refer to an amino acid polymer that has been modified through, for example, acetylation, disulfide bond formation, glycosylation, lipidation, phosphorylation, pegylation, biotinylation, cross-linking, and/or conjugation (e.g., with a labeling component or ligand). Polypeptide sequences are displayed herein in the conventional N-terminal to C-terminal orientation, unless otherwise indicated.

As used herein, the term "amino acid" refers to natural and synthetic (unnatural) amino acids, including amino acid analogs, modified amino acids, peptidomimetics, glycine, and D or L optical isomers. The amino acids making up the peptide may be natural L-amino acids, although in some embodiments, D-amino acids may be present. Alternatively, one or more non-naturally occurring amino acids may be present in a peptide of the present disclosure. Such non-naturally occurring amino acids include derivatives of naturally occurring amino acids.

Additionally, peptides of the present disclosure also include those that are modified without affecting the sequence of the peptide, e.g. by chemical modification. Examples of non-standard or structural analogue amino acids which can be incorporated into peptides include N-methyl amide, retro-inverse amide, thioamide, thioester, phosphonate, ketomethylene, hydroxymethylene, fluorovinyl, L-N methylamino acids, and D-N-methylamino acids.

The terms "fusion protein" and "chimeric protein" as used herein refer to a single protein created by joining two or more proteins, protein domains, or protein fragments that do not naturally occur together in a single protein.

A fusion protein can also comprise epitope tags (e.g., histidine tags, FLAG® (Sigma Aldrich, St. Louis, MO) tags, Myc tags), or reporter protein sequences (e.g., glutathione-S-transferase, beta-galactosidase, luciferase, green fluorescent protein, cyan fluorescent protein, yellow fluorescent protein). In some embodiments, linker or spacer nucleic acid or amino acid sequences are used to join two or more proteins, protein domains, or protein fragments.

The terms "wild-type," "naturally occurring," and "unmodified" are used herein to mean the typical (or most common) form, appearance, phenotype, or strain existing in nature; for example, the typical form of cells, organisms, polynucleotides, proteins, macromolecular complexes, genes, RNAs, DNAs, or genomes as they occur in, and can be isolated from, a source in nature. The wild-type form, appearance, phenotype, or strain serve as the original parent before an intentional modification. Thus, mutant, variant, engineered, recombinant, and modified forms are not wild-type forms.

By "isolated" it is meant, when referring to a polypeptide for example, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means that at least 75% by weight, more preferably at least 85% by weight, more preferably still at least 95% by weight, and most preferably at least 98% by weight, of the same molecule is present.

The terms "engineered," "genetically engineered," "genetically modified," "recombinant," "modified," "non-naturally occurring," and "non-native" indicate intentional human manipulation of the genome of an organism or cell. The terms encompass methods of genomic modification that include genomic editing, as defined herein, as well as techniques that alter gene expression or inactivation, enzyme engineering, directed evolution, knowledge-based design, random mutagenesis methods, gene shuffling, codon optimization, and the like. Methods for genetic engineering are known in the art.

The term "segment" as used herein in reference to an amino acid sequence refers to a contiguous sequence of amino acids that may be 10, 12, 15, 20, 25, 50, or 100 amino acid residues in length. As used herein, the term "heterologous," when used with reference to portions of a protein or nucleic acid sequence, indicates that the sequence comprises two or more subsequences that are not usually found in nature in the same relationship to each other. In one example, the heterologous sequences are from different species of bacteria. In another example, heterologous sequences are from different strains of the same species of bacteria. In one aspect, the heterologous sequences are from different species of *Enterococcus*, such as *E. faecalis, E. faecium, E. gallinarum, E. casseliflavus, E. avium, E. cecorum, E. durans, E. hirae, E. malodoratus, Enterococcus mundtii, E. pseudoavium* or *E. raffinosus*; or from different strains of the same species of *Enterococcus*.

In another aspect the heterologous sequences are from a bacterium and a bacteriophage or prophage, or from a bacterium and a synthetic, non-natural sequence of DNA.

The heterologous RBP may be comprised of all or part of an RBP obtained from another strain of the same species of *Enterococcus*, another species of *Enterococcus*, or a genus of bacteria other than the species and strain of the bacteria from which the scaffold was derived. In some embodiments, the heterologous RBP is from a prophage or prophage remnant from the genome of a gram positive bacterium, or from a bacteriophage that infects a gram positive bacterium.

In some embodiments, the heterologous RBP is from an *Enterococcus* genome, a bacteriophage, a prophage insertion or a prophage remnant that is contained within an *Enterococcus* genome. In some embodiments thereof, the *Enterococcus* is *E. faecalis* or *E. faecium*.

A "prophage remnant" or prophage element or portion, refers to a sequence that encodes only a portion of a phage or discrete phage protein(s), rather than a full phage structure. Thus, in some embodiments, a prophage remnant may include, for example, sequence encoding an RBP and other structural proteins. In certain embodiments, the RBP is of a prophage or prophage remnant from the genome of a gram positive bacterium or an RBP of a bacteriophage that infects a gram positive bacterium. In one example, the gram positive bacterium is a species of *Clostridium, Staphylococcus, Streptococcus, Bacillus, Enterococcus,* or *Propionibacterium*. In some embodiments, the natural RBP of a natural enterocin may be replaced with a modified form of a native RBP.

A "native RBP" refers to a RBP having an amino acid sequence that is identical to an RBP isolated or cloned from an *Enterococcus*, or from another genus or species of bacteria, or from a bacteriophage, or from a prophage or prophage remnant.

Exemplary native RBPs include, for example, SEQ ID NOs: 16 and 21. In some embodiments, a modified RBP includes a change in the amino acid sequence of the RBP relative to a native RBP. Non-limiting examples of a change in amino acid sequence include substitution, insertion (or addition), or deletion of one or more amino acids that modifies the binding or stability properties of the RBP.

In particular embodiments, the modified form of a native RBP also results in an enterocin having a heterologous RBP and bactericidal spectrum that is different from an enterocin containing the corresponding unmodified or native RBP. In particular embodiments, the modified form is at least 80% identical to the native RBP. In other embodiments, the RBP has an amino acid sequence that is at least 85%, 88%, 89%, 90%, 95%, 96%, 97%, 98%, or at least 99% identical, to a native RBP; and the modified RBP results in an enterocin having a bactericidal spectrum that is different from an enterocin having the corresponding unmodified or native RBP.

Also provided are variant enterocins. Variant enterocins include those enterocins containing polypeptides that are at least 80% identical to the polypeptides of SEQ ID NOs: 4-14, SEQ ID NOs: 4-15, or SEQ ID NOs: 4-16. In other embodiments, variant enterocins include enterocins containing polypeptides that are at least 85%, 86%, 87%, 88%, 89%, 90%, 91%, 92%, 93%, 94%, 95%, 96%, 97%, 98%, or at least 99% identical, to the polypeptides of SEQ ID NOs: 4-14, SEQ ID NOs: 4-15, or SEQ ID NOs: 4-16. In some embodiments, any one or more of the polypeptides in the variant enterocin may have at least 80%, 85%, 86%, 87%, 88%, 89%, 90%, 91%, 92%, 93%, 94%, 95%, 96%, 97%, 98%, or at least 99% identity, to the corresponding polypeptide(s) in a native enterocin, such as that encoded by *E. faecalis* isolate S32.

Also provided are vectors or expression constructs containing a nucleic acid molecule(s) encoding an enterocin. In some embodiments, the nucleic acid molecule(s) is operably linked to a heterologous inducible promoter in the vector or expression construct. In particular embodiments, the heterologous promoter is a small molecule induced promoter. Examples of such small molecule induced promoters include $P_{LAC}$ (lactose, IPTG), PTAC (IPTG), $P_{BAD}$ (arabinose), and $P_{XYL}$ (Xylose).

In some embodiments, the promoter is placed at approximately 11, 14, 17, 20, or 23 nucleotides upstream of the portion of a polynucleotide sequence encoding SEQ ID NO: 4, or of a polynucleotide sequence encoding a polypeptide at least 80%, 85%, 86%, 87%, 88%, 89%, 90%, 91%, 92%, 93%, 94%, 95%, 96%, 97%, 98%, or at least 99% identical, to SEQ ID NO: 4.

In other embodiments, the vector or expression construct may include one or more regulatory or accessory proteins encoded by an enterocin genetic locus or gene cluster. In particular embodiments, the one or more regulatory or accessory proteins include, for example, Genes 1276, 1277, 1292 and 1293 of *E. faecalis* isolate S32; or corresponding genes in other *Enterococcus* species, bacteria, prophages, prophage remnants, or bacteriophages. In some embodiments, the one or more regulatory or accessory proteins include, for example, SEQ ID NOs: 2, 3, 17 and 18.

An enterocin of the invention may be cold active, that is, it has bactericidal activity in cold temperatures, such as 2-10° C.

An additional property common to the enterocins disclosed herein is that they do not contain nucleic acid, and thus, are replication deficient such that they cannot reproduce themselves after or during the killing of a target bacterium, as can many bacteriophages. They are purely proteins, not organisms or viruses.

A "target bacterium" or "target bacteria" refers to a bacterium or bacteria that are bound by an enterocin of the disclosure and/or whose growth, survival, or replication is inhibited thereby. In some embodiments, the target bacterium is from the genus *Enterococcus*. In some embodiments, the target bacterium is from a species of *Enterococcus* selected from the group consisting of *E. faecalis, E. faecium, E. gallinarum, E. casseliflavus, E. avium, E. cecorum, E. durans, E. hirae, E. malodoratus, E. mundtii, E. pseudoavium* and *E. raffinosus*.

In certain aspects, one, or more than one, strain of *E. faecium* and/or *E. faecalis* is targeted. Exemplary strains of *E. faecium* include, but are not limited to, strain M27, M28, M29, M30, M31, M32, M33, M34 and M35. Exemplary strains of *E. faecalis* include, but are not limited to, strain S25, S29, S30, S31, S32, S33, S34, S35, S36, 108, 109, 13589 and 13590.

In some embodiments, the target bacterium is from a different genus of gram-positive bacteria, such as, for example, *Clostridium, Staphylococcus, Streptococcus, Bacillus, Enterococcus,* or *Propionibacterium*. The term "growth inhibition" or variations thereof refers to the slowing or stopping of the rate of a bacterial cell's division or cessation of bacterial cell division, or to the death of the bacterium or bacteria.

Also provided are methods of treating an infection with *Enterococci* in an animal, by administering to an animal in need thereof an amount of an enterocin, or an enterocin producer cell to produce a bactericidal amount of the enterocin, thereby treating the infection. In some embodiments, the infection is with a species of *Enterococcus* selected from the group consisting of *E. faecalis, E. faecium, E. gallinarum, E. casseliflavus, E. avium, E. cecorum, E. durans, E. hirae, E. malodoratus, E. mundtii, E. pseudoavium* and *E. raffinosus*

As described herein, an anti-bacterial enterocin may be used to inhibit growth, survival, or replication of a particular bacterium. The bacterium may be a pathogenic or environmentally deleterious strain, or may be treated in a prophylactic manner. A pathogenic microorganism generally causes disease, sometimes only in particular circumstances.

An engineered enterocin of the disclosure may be administered to any subject afflicted with, diagnosed as afflicted with, or suspected of being afflicted with, an infection, colonized by, or contamination by bacteria susceptible to the enterocin. Non-limiting examples of such a subject include animal (mammalian, reptilian, amphibian, avian, and fish) species as well as insects, plants and fungi. Representative, and non-limiting, examples of mammalian species include humans; non-human primates; agriculturally relevant species such as cattle, pigs, goats, and sheep; rodents, such as mice and rats; mammals for companionship, display, or show, such as dogs, cats, guinea pigs, rabbits, and horses; and mammals for work, such as dogs and horses. Representative, and non-limiting, examples of avian species include chickens, ducks, geese, and birds for companionship or show, such as parrots and parakeets. An animal subject treated with an engineered enterocin of the disclosure may also be a quadruped, a biped, an aquatic animal, a vertebrate, or an invertebrate, including insects.

In some embodiments, the subject in need to be treated is a human child or fetus or other young animal which has yet to reach maturity. Thus the disclosure includes the treatment of pediatric or obstetric conditions comprising infection with bacteria or other microorganism susceptible to an enterocin of the disclosure.

In some embodiments, there are provided compositions of more than one non-natural enterocin, wherein the non-natural enterocins have differing bactericidal spectra. In other embodiments, there are provided compositions of one or more non-natural enterocins and one or more natural enterocins, wherein the enterocins have differing bactericidal spectra.

Enterocin-containing compositions of the present disclosure may further comprise an additional antibacterial agent. Antibacterial agents in this context refer to agents which are able to kill one or more bacteria, though not necessarily with the same potency as the enterocins of the present disclosure. Appropriate agents include other PTLBs, bacteriocins, or antibiotics. Suitable antibiotics include penicillins (such as penicillin and amoxicillin), cephalosporins (such as cephalexin (Keflex)), macrolides (such as erythromycin (E-Mycin), clarithromycin (Biaxin) and azithromycin (Zithromax)), fluoroquinolones (such as ofloxacin (Cipro), levofloxacin (Levaquin) and ofloxacin (Floxin)), sulfonamides (such as co-trimoxazole (Bactrim) and trimethoprim (Proloprim)), tetracyclines (such as tetracycline (Sumycin, Panmycin) and doxycycline (Vibramycin)) and aminoglycosides (such as gentamicin (Garamycin) and tobramycin (Tobrex)).

In some embodiments, enterocins, combinations of enterocins, or enterocin producer cells capable of producing enterocins, are formulated with a "pharmaceutically acceptable" excipient, enteric coating or carrier. Such a component is one that is suitable for use with humans, animals, and/or plants without undue adverse side effects. Non-limiting examples of adverse side effects include toxicity, irritation, and/or allergic response. The excipient or carrier is typically one that is commensurate with a reasonable benefit/risk ratio. Non-limiting pharmaceutically suitable carriers include sterile aqueous or non-aqueous solutions, suspensions, and emulsions. Examples include, but are not limited to, standard pharmaceutical excipients such as a phosphate buffered saline solution, bicarbonate solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Additional formulations and pharmaceutical compositions disclosed herein comprise an isolated enterocin specific for a bacterial pathogen; a mixture of two, three, five, ten, or twenty or more different enterocins or producer cells capable of producing enterocin that target the same bacterial pathogen; and a mixture of two, three, five, ten, or twenty or more that target different bacterial pathogens or different strains of the same bacterial pathogen.

Optionally, a composition comprising an enterocin or producer cell of the disclosure may also be spray dried or lyophilized using means well known in the art. Subsequent reconstitution and use may be practiced as known in the field.

An enterocin is typically used in an amount or concentration that is "safe and effective," which refers to a quantity that is sufficient to produce a desired therapeutic or prophylactic response without undue adverse side effects like those described above. An enterocin may also be used in an amount or concentration that is "therapeutically effective," which refers to an amount effective to yield a desired therapeutic response, such as, but not limited to, an amount effective to slow the rate of bacterial cell division, or to cause cessation of bacterial cell division, or to cause death or decrease rate of population growth of the target bacteria. The safe and effective amount or therapeutically or prophylactically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

"Treatment" or "treating" a particular disease includes: (1) preventing the disease, for example, preventing the development of the disease or causing the disease to occur with less intensity in a subject that may be predisposed to the disease, but does not yet experience or display symptoms of the disease; (2) inhibiting the disease, for example, reducing the rate of development, arresting the development or reversing the disease state; and/or (3) relieving symptoms of the disease, for example, decreasing the number of symptoms experienced by the subject.

The terms "producer cell" and "enterocin producer cell" are used interchangeably herein and refer to a cell that is capable of producing or expressing an enterocin-encoding nucleic acid molecule, and which does not naturally contain such a nucleic acid molecule. The producer cell may be capable of surviving and growing in the presence of oxygen and is transformed with a vector containing a nucleic acid molecule encoding the enterocin, which may be integrated into the chromosome of the producer cell or may be episomal. The producer cell may be a gram-positive bacterium. In certain embodiments, the producer cell may be a bacterium from the genus *Bacillus, Lactobacillus, Listeria,* or *Lactococcus.*

In some embodiments, the bacterium is a species from the genus *Bacillus* selected from the group consisting of *B. subtilis, B. amyloliquefaciens,* and *B. megaterium.* In one aspect, the bacterium is *B. subtilis*. In a particular aspect, the producer cell is a *B. subtilis* strain that lacks the PBSX gene cluster SpoA, Flag, etc. In other embodiments, the bacterium is a species from the genus *Lactobacillus* selected from the group consisting of *L. acidophilus, L. casei,* and *L. bulgaricus*.

The term "comprising", which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

The following examples are intended to illustrate but not limit the invention.

Example 1

Cloning and Expression of an Enterocin Gene Cluster

This example illustrates the identification of a genetic locus (pp2) within a strain of *E. faecalis* that encodes an enterocin.

The enterocin gene cluster was previously described as a "prophage" by bioinformatic inspection of the genome sequence of *E. faecalis* strain V583. See Matos et al. ("*Enterococcus faecalis* prophage dynamics and contributions to pathogenic traits," *PLOS Genet.,* 2013, 9(6): e1003539). However, the present inventors identified the existence of very similar gene clusters, pp2-like loci, in many other, if not all, *E. faecalis* strains, raising the possibility that the pp2 locus was not a prophage.

To determine whether the pp2- and pp2-like loci encoded a PTLB, *E. faecalis* isolate S32 was selected as a representative source. SEQ ID NO: 1 is the DNA sequence that encoded the enterocin. The amino acid sequences of the proteins associated with the enterocin locus are shown in SEQ ID NOs: 2-17.

The DNA sequence from genes 1278 (SEQ ID NO: 4) through 1291 (SEQ ID NO: 16) was cloned using primers based on the V583 sequence. See Matos et al. ("*Enterococcus faecalis* prophage dynamics and contributions to pathogenic traits," *PLOS Genet.,* 2013, 9(6): e1003539). Genes 1276 and 1277 (SEQ ID NOs: 2-3) were not included, as they were predicted by the present inventors to encode regulatory proteins needed only in the natural context. Additionally, Genes 1292 and 1293 (SEQ ID NOs: 17-18) were not included, since these genes were predicted to encode a holin and a lysozyme, respectively (and would potentially lyse producer cells upon expression). FIG. 1 depicts the structure of the S32 enterocin genetic locus cloned and expressed in *B. subtilis*.

Gene 1391, based on its context within the enterocin gene cluster, was predicted by the present inventors to be the RBP, a critical component of a bacteriocin for recognizing and binding specific surface targets on the target bacteria.

Figure 2A:
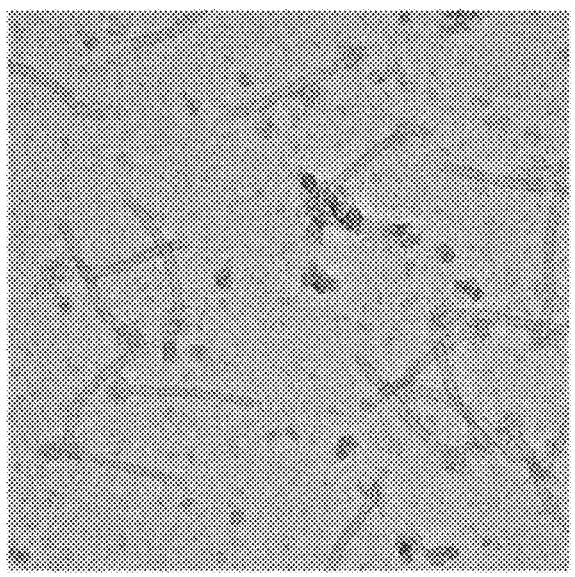
FIGS. 2A and 2B.
Figure 2B:
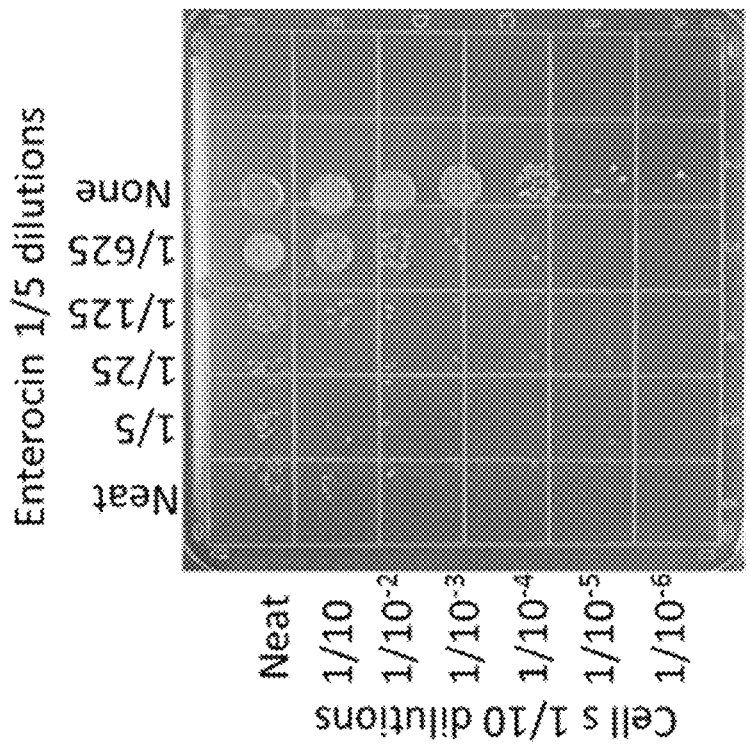

The DNA encoding genes 1278-1291 was inserted into a pETcoco-based bacterial artificial chromosome with flanking sequences to allow integration of the gene cluster specifically into the amyE gene of the *B. subtilis* genome. See Lee et al. ("F-type bacteriocins of *Listeria monocytogenes*: a new class of phage tail-like structures reveals broad parallel coevolution between tailed bacteriophages and high-molecular-weight bacteriocins," *J. Bacteriol.,* 2016, 198(20): 2784-93). Downstream of the enterocin gene cluster, but still within the flanking amyE sequences, the CAT gene was inserted to enable selection of *B. subtilis* integrants with chloramphenicol. To induce expression of the enterocin genes, the $P_{hyperspank}$ promoter was placed immediately upstream of gene 1278. This entire DNA construct was termed DG1119. The $P_{hyperspank}$ promoter was inducible by the addition of IPTG, and in this context, was predicted to drive expression of all of the putative enterocin genes. DG1119 was introduced into *B. subtilis* strain Δ8 by electroporation. The flanking amyE sequences allowed integration by homologous recombination of the enterocin gene cluster and the CAT gene within the bacterial amyE gene. See Lee et al. ("F-type bacteriocins of *Listeria monocytogenes*: a new class of phage tail-like structures reveals broad parallel coevolution between tailed bacteriophages and high-molecular-weight bacteriocins," *J. Bacteriol.,* 2016, 198(20): 2784-93). Transformants were selected on chloramphenicol plates and screened for the presence of the integrated enterocin gene cluster. The positive integrant was termed BDG477. To test enterocin-producing ability, BDG477 was grown in liquid culture, and the expression of the enterocin genes was induced by the addition of IPTG to the medium. After overnight incubation, the cells were collected, lysed, and putative enterocin particles were purified by ultracentrifugation using previously described methods. See Lee et al. ("F-type bacteriocins of *Listeria monocytogenes*: a new class of phage tail-like structures reveals broad parallel coevolution between tailed bacteriophages and high-molecular-weight bacteriocins," *J. Bacteriol.,* 2016, 198(20): 2784-93). Enterocins produced from BDG477 were examined by electron microscopy and showed the structure of a novel F-type bacteriocin. See FIG. 2A. This novel PTLB was named enterocin AV-S32. Bactericidal activity of AV-S32 was tested by both the spot assay method and the survival assay method, see Williams et al. ("Retargeting R-type pyocins to generate novel bactericidal protein complexes," *Appl. Environ. Microbiol.,* 2008, 74(12): 3868-76), the results of which are depicted in FIG. 2B. Briefly, ~$10^8$ of cells/ml of *E. faecium* M32 were incubated with different dilutions of an enterocin AV-S32 preparation. After a one-hour incubation, the cells were diluted serially 1/10; 10 μl of each dilution was spotted onto a nutrient agar plate; and the plate was allowed to incubate overnight until colonies were visible. No killing was noted in the sample that was not exposed to enterocins (column marked "none"). Dose-dependent bactericidal activity can be seen in the samples contacted with enterocins. The number of surviving cells will be based on the probability of a cell coming in contact with an enterocin particle at a given enterocin concentration and will follow a Poisson distribution.

The bactericidal spectrum on a panel of different *E. faecalis* and *E. faecium* strains is shown in FIG. 3. AV-S32 had bactericidal activity against isolates of both *E. faecalis* and *E. faecium,* 2 distinct species of the *Enterococcus* genus.

Example 2

Engineering the Bactericidal Spectrum of Enterocin

Figure 4:
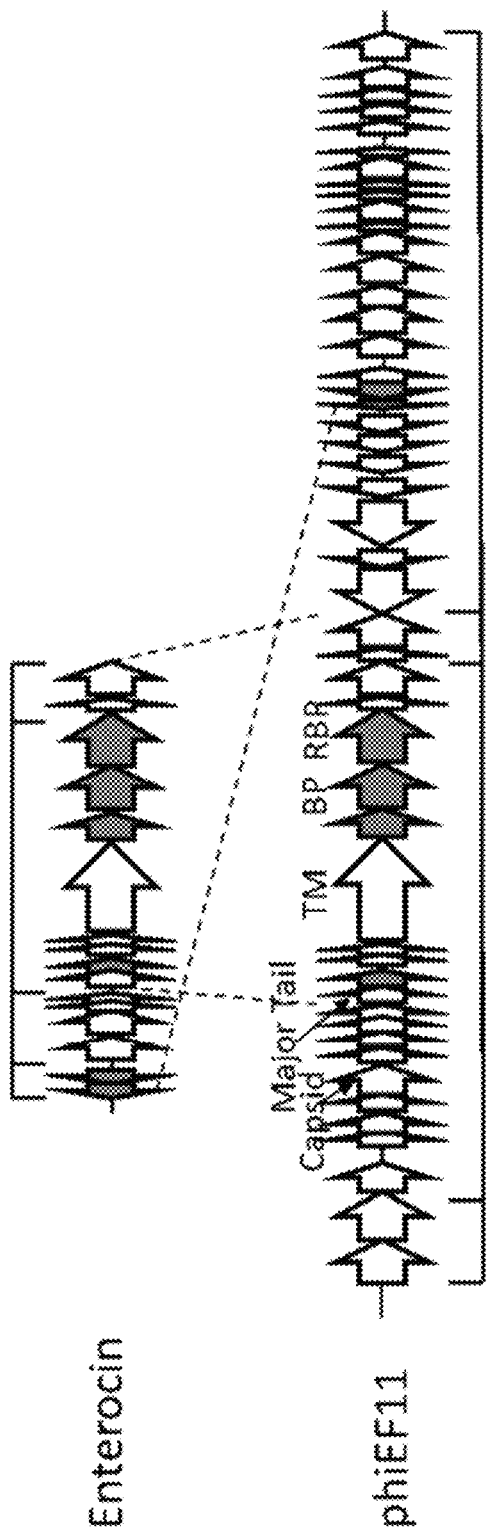
FIG. 4. Comparison of the enterocin gene cluster and the genome of phiEF11. BP is the BPAR, RBP is the receptor binding protein, and TM is the tape measure.

As wild-type enterocin did not have a sufficient broad spectrum within *Enterococcus* sps. to be a promising therapeutic, experiments were performed to change and/or expand the bactericidal activity to cover diverse clinical isolates of *Enterococci*. The spectra of PTLBs are determined by their RBP, see Scholl et al. ("Phage tail-like bacteriocins," *Annu. Rev. Virology*, 2017, 29: 453-467), so experiments were undertaken to modify the RBP. Whilst some PTLBs contain a "Base Plate Attachment Region" (BPAR; which mediates binding of the RBP to the baseplate) within the RBP itself, the present inventors determined that enterocins, including AV-S32, utilize an adaptor protein (e.g., gene 1290) that contains the BPAR, but which is encoded by a different ORF from the ORF encoding the RBP (e.g., gene 1291). The adaptor protein consisted of two domains, an N-terminal "Base Plate Attachment Region" or BPAR, and a C-terminal region that interacts with the RBP. The gene product of gene 1290 in *E. faecalis* isolate S32 acted as an adaptor between the enterocin's baseplate and the RBP. Thus, to link the scaffold of the enterocin to a heterologous RBP, the RBP-interacting region of the adaptor protein (i.e., the protein encoded by Gene 1290) was adapted to allow a heterologous RBP to be linked to the enterocin scaffold via this modified RBP adaptor protein. To this end, the present inventors identified a family of phages related to *E. faecalis* phage phiEF11, which contained genes analogous to those encoding tail structures of enterocin AV-S32. See FIG. 4. This family of phages was referred to as phiEF11-like phages. Three of the predicted proteins from phiEF11-like phages shared significant sequence similarity to the enterocin proteins. Furthermore, one of these proteins was identified by the present inventors as a putative RBP, analogous to enterocin gene 1291. Another of these proteins was a putative RBP adaptor protein, analogous to enterocin gene 1290.

The PhiEF11-like phages had putative RBPs that were highly divergent from that of enterocin AV-S32, suggesting that they targeted different strains of *Enterococcus* than did AV-S32. Moreover, the corresponding C-terminal region of the RBP adaptor protein of PhiEF11-like phages was also divergent, suggesting its interaction with its cognate RBP. From these discoveries, the present inventors predicted that phage RBPs could be incorporated into an enterocin via the enterocin's baseplate and scaffold, to thereby produce novel enterocins with bactericidal activity redirected to *Enterococcus* species and strains, of at least *E. faecalis* and *E. faecium* species, that were naturally infected by the phage (s).

To do this, the present inventors engineered the enterocin RBP adaptor protein, in order to accommodate the new RBP (since the BPAR at the N-terminal portion of the RBP adaptor protein is required to interact with the enterocin baseplate; and the C-terminus of the RBP adaptor protein interacts with its cognate RBP). Thus, in order to have a foreign or heterologous RBP incorporated into the enterocin structure, it must interact with the C-terminus of its cognate RBP adaptor protein which in turn must be fused to the N-terminus of the enterocin's BPAR in order to properly link the enterocin's baseplate structure.

To validate this approach, a ph1EF11-like prophage encoded in *E. faecium* strain CUN41 (termed prophage phiCUN41) was selected. The putative BPAR of phiCUN41 was encoded by ORF4630 (SEQ ID NO: 19). The putative RBP of phiCUN41 was encoded by ORF4620 (SEQ ID NO: 21). A short DNA sequence was annotated as a small ORF (SEQ ID NO: 20) but possibly was not translated. Downstream of the putative RBP were two additional ORFs (ORFs 4615 and 4610; SEQ ID NOs: 22-23, respectively). The present inventors predicted that these three two ORFs were important for RBP assembly and/or function.

Figure 5:
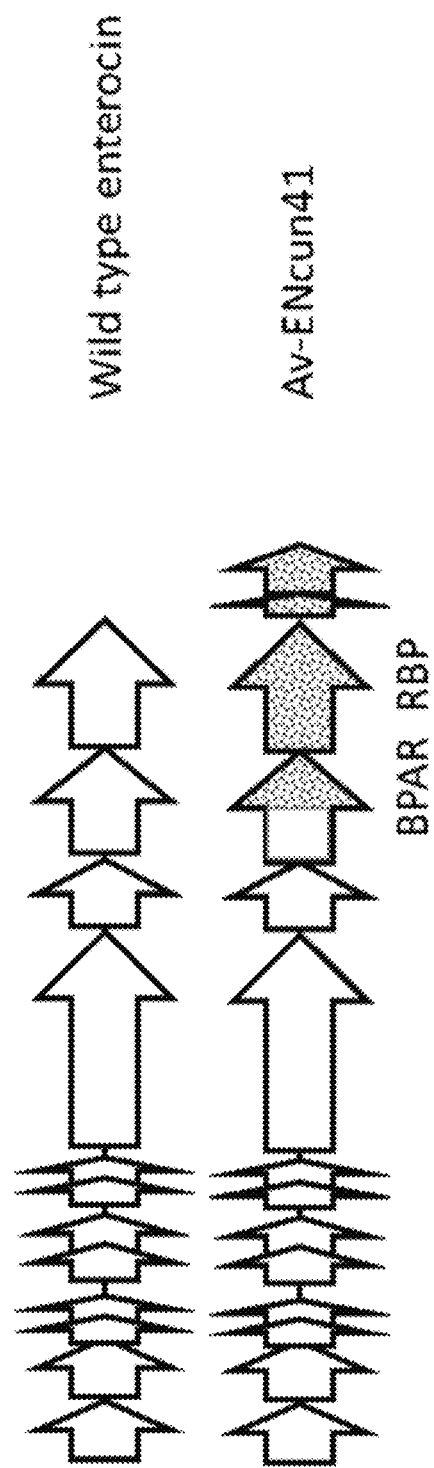
FIG. 5.

The DNA encoding this entire region was synthesized, and a fusion was made between the DNA encoding the enterocin's RBP adaptor and the DNA encoding these phiCUN41 genes. The fusion site was placed within the RBP adaptor genes at amino acid position 364 (position 364 in both genes), which was predicted to be the boundary between the BPAR region and the RBP-binding region. Accordingly, the N-terminal 364 amino acid portion of the enterocin's adaptor protein (BPAR-containing region) interacted with the upstream genes encoding the enterocin's baseplate and scaffold; whereas the C-terminal portion (residues 365-689) of the phiCUN adaptor protein interacted with the phage RBP and the products of ORFs 4620, 4615 and 4610. See FIG. 5. As such, the resulting construct consisted of the enterocin scaffold and up to amino acid 364 of the enterocin's BPAR (within the enterocin adaptor protein), at which point it was fused to the RBP-binding region of the phage RBP adaptor protein, along with the downstream genes needed for RBP attachment and function. This novel bacteriocin was termed "Av-ENcun41."

The Av-ENcun41 DNA construct was integrated into the *B. subtilis* genome, and IPTG-induced particles were collected and purified. The bactericidal spectrum was tested against the same panel of strains used to test AV-S32 enterocin. The spectrum of Av-ENcun41 was distinct and notably killed many more *E. faecium* strains. See FIG. 3.

Example 3

Figure 6:
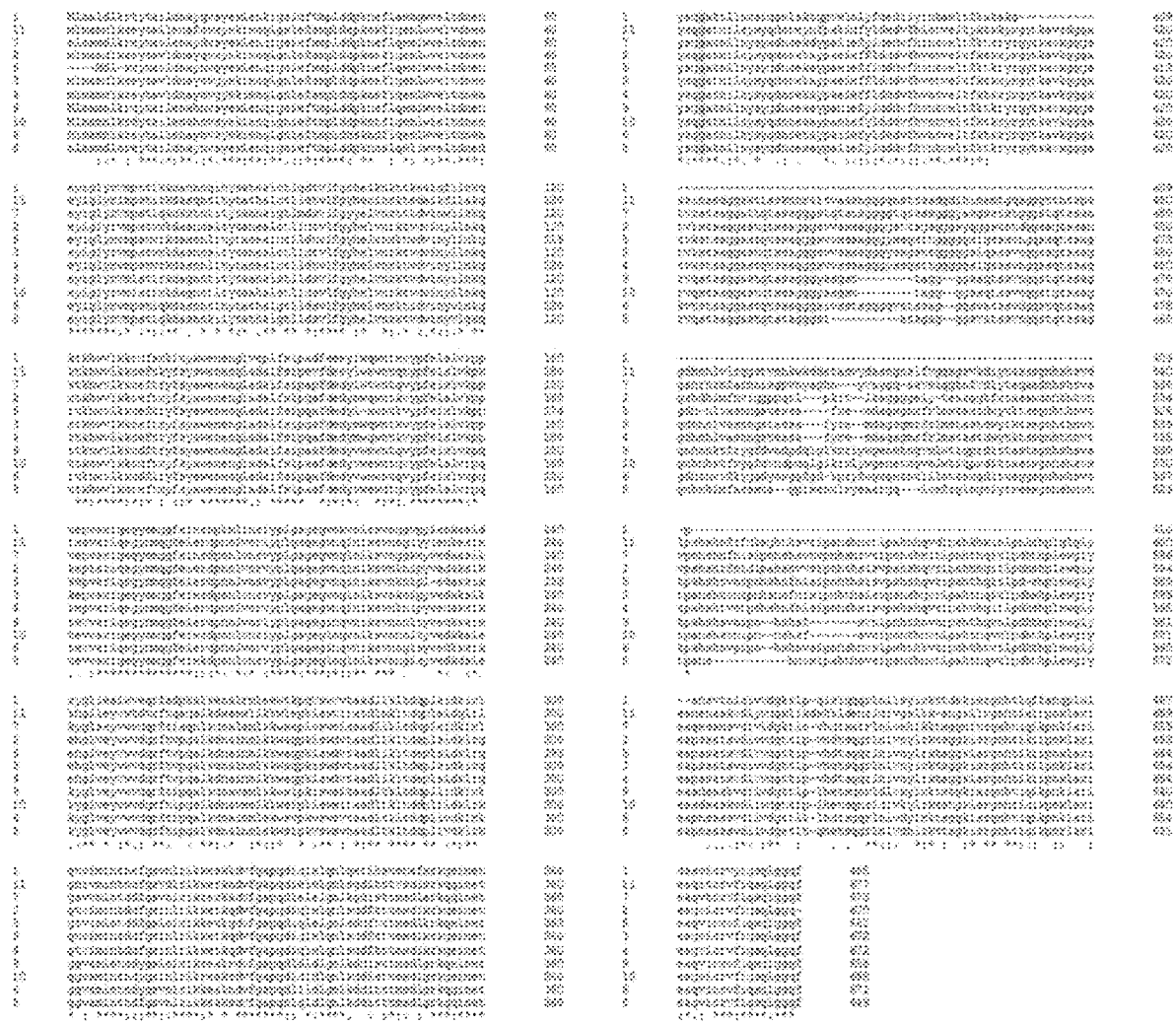
FIG. 6. Multiple sequence alignment of the enterocin BPAR with the BPARs of phiEF11-like phages/prophages predicted by the present inventors. The N-terminal domains of all of these proteins are highly conserved; whereas in contrast, the bulk of the C-terminal domains are divergent. The highlighted residues are amino acids 364 and 365, the site where the functional fusion was made to create Av-ENcun41. The immediate neighbors of the successful fusion site of Av-ENcun41 are nearly identical in all of these prophase/phages. Therefore, the same method can be used for the BPARs of all the phiEF11 phages/prophages to create a collection of enterocins with highly diverse binding and bactericidal spectra. The source of the BPAR sequences numbered and shown in FIG. 5 are 1) Enterocin; 2) phiEF11; 3) Phage vB_EfaS; 4) Phage EFC-1; 5) Phage FC1; 6) *Enterococcus silesiacus* prophage; 7) *Enterococcus mediterraneensis* prophage; 8) *Enterococcus plantarum* prophage; 9) *Enterococcus moraviensis* prophage; 10) *Enterococcus wangshanyuanii* prophage; and 11) *Enterococcus pallens* prophage.

Engineering the Expansion of Enterocin Spectra by Deploying all PhiEF11 Phages/Prophages A comparison of the RBP adaptors from 9 additional phiEF11 phages/prophages was conducted. See FIG. 6. This analysis revealed that the N-terminal BPAR domains of all of these adaptor proteins are conserved; and that the C-terminal RBP-binding domains are highly divergent. These unique observations were consistent with their requirement for attachment of the different RBPs to the phage baseplate via the intermediary conserved N-terminal domain of their cognate RBP adaptor; and to their unique targeting molecule, RBP, via their highly diverse C-terminal domain of the cognate BPAR-containing adaptor proteins. Importantly, it was discovered by the present inventors that the immediate region around amino acid 364 of the RBP adaptors in all of the phiEF11 phages/prophages was identical. This thereby will enable the generation of many hybrid enterocins, with different and distinct binding and killing spectra, by engineering techniques as described in Example 2 herein, e.g., using each of these C-terminal domains of adaptor proteins of phiEF11 phages/prophages, and deploying the engineered RBP adaptors along with their highly diverse RBPs as unique components for novel enterocins.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Although the invention has been described with reference to the above example, it will be understood that modifications and variations are encompassed within the spirit and scope of the invention. Accordingly, the invention is limited only by the following claims.

What is claimed is:

1. An isolated nucleic acid molecule encoding an enterocin, wherein the nucleic acid molecule comprises a first polynucleotide sequence that encodes the structural proteins of a functional enterocin except the corresponding natural receptor binding protein (RBP) and the corresponding natural base plate attachment region-containing (BPAR-containing) adaptor protein; wherein the structural proteins encoded by the first polynucleotide sequence are at least 80% identical to SEQ ID NOs: 4-14; wherein the nucleic acid molecule further comprises a heterologous second polynucleotide sequence encoding a heterologous RBP; and wherein the enterocin has bactericidal specificity against at least one strain of an *Enterococcus* species, or other genus of bacteria, as determined by the heterologous RBP, and the bactericidal specificity is different from that determined by the natural RBP of the natural enterocin.

2. The nucleic acid molecule of claim 1, wherein said nucleic acid molecule further comprises a third polynucleotide sequence encoding a heterologous adaptor protein, wherein said heterologous adaptor protein links said heterologous RBP to the structural proteins encoded by said first polynucleotide sequence; and wherein said heterologous adaptor protein comprises a BPAR native to the structural proteins encoded by the first polynucleotide sequence.

3. The nucleic acid molecule of claim 2, wherein the BPAR is located at or towards the N-terminus of said heterologous adaptor protein.

4. The nucleic acid molecule of claim 2, wherein the heterologous adaptor protein includes an amino acid sequence at least 80% identical to residues 1-369 of SEQ ID NO: 15.

5. The nucleic acid molecule of claim 2, wherein the encoded heterologous adaptor protein further comprises at least a part of an adaptor protein of a prophage or prophage remnant from the genome of a gram positive bacterium; or comprises at least a part of an adaptor protein of a bacteriophage that infects a gram positive bacterium.

6. The nucleic acid molecule of claim 5, wherein said part of an adaptor protein of a prophage or prophage remnant from the genome of a gram positive bacterium, or said part of an adaptor protein of a bacteriophage that infects a gram positive bacterium, is located at or towards the C-terminus of said heterologous adaptor protein.

7. A vector comprising the nucleic acid molecule of claim 1, wherein the nucleic acid molecule is operably linked to a small molecule-induced promoter.

8. The vector of claim 7, wherein the promoter is placed at 11, 14, 17, 20, or 23 nucleotides upstream of the portion of the nucleic acid encoding a polypeptide at least 80% identical to SEQ ID NO: 4.

9. An isolated nucleic acid molecule encoding an enterocin, wherein the nucleic acid molecule comprises a first polynucleotide sequence that encodes polypeptides at least 80% identical to SEQ ID NOs: 4-16, operably linked to a heterologous promoter inducible by a small molecule; wherein the encoded enterocin has bactericidal activity against at least one strain of an *Enterococcus* species; and wherein the first polynucleotide sequence is operably linked to the heterologous promoter.

10. The nucleic acid molecule of claim 9, wherein the promoter is placed at 11, 14, 17, 20, or 23 nucleotides upstream of the portion of the nucleic acid encoding a polypeptide at least 80% identical to SEQ ID NO: 4.

11. An enterocin producer cell comprising a first foreign polynucleotide sequence that encodes structural polypeptides at least 80% identical to SEQ ID NOs: 4-14, and further comprising a second foreign polynucleotide sequence encoding a heterologous RBP; wherein the bactericidal specificity of the enterocin is determined by the heterologous RBP; and wherein the first and second foreign polynucleotide sequences are located in the same nucleic acid molecule or are located in separate nucleic acid molecules.

12. A producer cell of claim 11, wherein the first and second foreign polynucleotide sequences are in separate nucleic acid molecules.

13. The producer cell of claim 11, wherein said producer cell further comprises a third foreign polynucleotide sequence encoding a heterologous adaptor protein, wherein said heterologous adaptor protein links said heterologous RBP to the structural proteins encoded by said first polynucleotide sequence, and wherein said heterologous adaptor protein comprises a BPAR native to the structural proteins encoded by the first polynucleotide sequence.

14. The producer cell of claim 13, wherein the BPAR is located at or towards the N-terminus of said heterologous adaptor protein.

15. The producer cell of claim 13, wherein the heterologous adaptor protein includes an amino acid sequence at least 80% identical to residues 1-369 of SEQ ID NO: 15.

16. The producer cell of claim 13, wherein the encoded heterologous adaptor protein further comprises at least a part of an adaptor protein of a prophage or prophage remnant from the genome of a gram positive bacterium; or comprises at least a part of an adaptor protein of a bacteriophage that infects a gram positive bacterium.

17. The producer cell of claim 16, wherein said part of an adaptor protein of a prophage or prophage remnant from the genome of a gram positive bacterium, or said part of an adaptor protein of a bacteriophage that infects a gram positive bacterium, is located at or towards the C-terminus of said heterologous adaptor protein.

18. An enterocin encoded by a nucleic acid molecule comprising a first polynucleotide sequence that encodes structural proteins of a functional enterocin except the corresponding natural receptor binding protein (RBP) and the corresponding natural base plate attachment region-containing (BPAR-containing) adaptor protein; wherein the structural proteins encoded by the first polynucleotide sequence are at least 80% identical to SEQ ID NOs: 4-14; wherein the nucleic acid molecule further comprises a heterologous second polynucleotide sequence encoding a heterologous RBP; and wherein the enterocin has bactericidal specificity against at least one strain of an *Enterococcus* species, or other genus of bacteria, as determined by the heterologous RBP, and the bactericidal specificity is different from that determined by the natural RBP of the natural enterocin.

19. A method of killing an *Enterococcus* species in vivo, comprising contacting the *Enterococcus* with an effective amount of the enterocin of claim 18, whereby the enterocin binds and kills the *Enterococcus*.

20. The method of claim 19, wherein the contacting is to an *Enterococcus* on a surface contaminated with *Enterococcus*.

21. The nucleic acid molecule of claim 4, wherein the adaptor protein comprises amino acids identical to those at positions 364 and 365 of SEQ ID NO: 15.

22. The enterocin of claim 18 for use in a method of treating an *Enterococcus* infection in an animal.

23. The producer cell of claim 11, for use in a method of treating an *Enterococcus* infection in an animal.

24. The enterocin of claim 18, wherein the enterocin has bactericidal specificity against at least one strain of an *Enterococcus* species as determined by the heterologous RBP.

25. The enterocin of claim 18, wherein the heterologous RBP is a modified native RBP.

26. The enterocin of claim 18, wherein the heterologous RBP is an RBP of PhiEF11-like phage.

27. The enterocin of claim 18, wherein the heterologous RBP is an RBP having a sequence at least 80% identical to SEQ ID NO: 16.

28. The enterocin of claim 18, wherein the heterologous RBP is an RBP having a sequence at least 95% identical to SEQ ID NO: 16.

29. The enterocin of claim 18, wherein the heterologous RBP is an RBP of SEQ ID NO: 16.

30. The enterocin of claim 18, wherein the heterologous RBP is an RBP having a sequence at least 80% identical to SEQ ID NO: 21.

31. The enterocin of claim 18, wherein the heterologous RBP is an RBP having a sequence at least 95% identical to SEQ ID NO: 21.

32. The enterocin of claim 18, wherein the heterologous RBP is an RBP of sequence of SEQ ID NO: 21.

33. The enterocin of claim 18, wherein the structural proteins encoded by the first polynucleotide sequence are the structural proteins of SEQ ID NOs: 4-14.

* * * * *